US006883375B2

(12) United States Patent
Dunegan

(10) Patent No.: US 6,883,375 B2
(45) Date of Patent: Apr. 26, 2005

(54) DETECTION OF MOVEMENT OF TERMITES IN WOOD BY ACOUSTIC EMISSION TECHNIQUES

(76) Inventor: Harold L. Dunegan, 22812 Tamora Dr., Laguna Niguel, CA (US) 92677

( * ) Notice: Subject to any disclaimer, the term of this patent is extended or adjusted under 35 U.S.C. 154(b) by 0 days.

(21) Appl. No.: 10/716,077

(22) Filed: Nov. 18, 2003

(65) Prior Publication Data

US 2004/0107773 A1 Jun. 10, 2004

Related U.S. Application Data

(63) Continuation of application No. 10/189,283, filed on Jul. 1, 2002, now abandoned.
(60) Provisional application No. 60/316,721, filed on Aug. 30, 2001, and provisional application No. 60/302,419, filed on Jun. 29, 2001.

(51) Int. Cl.[7] ............................................. G01N 29/04
(52) U.S. Cl. ...................................................... 73/587
(58) Field of Search .......................... 73/587, 591, 584, 73/602; 367/136, 139, 180

(56) References Cited

U.S. PATENT DOCUMENTS

| | | | |
|---|---|---|---|
| 4,510,812 A | 4/1985 | Feng ............................. | 73/644 |
| 4,809,554 A | 3/1989 | Shade et al. ................... | 73/587 |
| 4,895,025 A | 1/1990 | Betts ............................. | 73/587 |
| 4,937,555 A * | 6/1990 | Litzkow et al. .............. | 340/540 |
| 4,941,356 A | 7/1990 | Pallaske ....................... | 73/587 |
| 4,991,439 A | 2/1991 | Betts ............................. | 73/587 |
| 5,014,556 A | 5/1991 | Dunegan ....................... | 73/587 |
| 5,285,688 A | 2/1994 | Robbins et al. ............... | 73/587 |
| 5,473,942 A | 12/1995 | Vick et al. ..................... | 73/587 |
| 5,616,845 A * | 4/1997 | Hickling et al. .............. | 73/584 |
| 5,714,687 A | 2/1998 | Dunegan ....................... | 73/587 |
| 5,877,422 A * | 3/1999 | Otomo .......................... | 73/587 |
| 5,929,315 A | 7/1999 | Dunegan ....................... | 73/182 |
| 6,041,656 A | 3/2000 | Dunegan ....................... | 73/587 |
| 6,062,083 A | 5/2000 | Dunegan ....................... | 73/587 |
| 6,173,613 B1 | 1/2001 | Dunegan ....................... | 73/587 |
| 6,360,608 B1 | 3/2002 | Dunegan ....................... | 73/587 |

FOREIGN PATENT DOCUMENTS

| | | | |
|---|---|---|---|
| DE | 2313833 A | 10/1974 | |
| JP | 08051908 A * | 2/1996 | ............ A01M/1/00 |

OTHER PUBLICATIONS

Evaluation of a Novel, Hand–Held, Acoustic Emissions Detector to Monitor Termites (Isoptera; Kalotermitidae, Rhinotermitdae) in Wood by Rudolf H. Scheffrahn et al., 1993 Entomological Society of America, pp. 1720–1729 (Dec. 1993).

"Detection of Termites with Acoustic Emission" by Richard L. Lemaster et al., Forest Products Journal, vol. 47, No. 2, pp. 75–79.

* cited by examiner

*Primary Examiner*—Hezron Williams
*Assistant Examiner*—Rose M. Miller
(74) *Attorney, Agent, or Firm*—Knobbe, Martens, Olson & Bear LLP

(57) ABSTRACT

Acoustic emission apparatus methods for detecting termite infestation including a probe and signal processing circuitry. The probe includes an piezoelectric transducer and is adapted to be inserted into a bore-hole of the wood under test. The waveguide intersects the high frequency extensional and shear waves produced by feeding and movement of termite propagating along the grain of the wood.

The transducer output signal is filtered through high (HF) and low (LF) bandbase filters. Selected HF/LF values produce a signal which substantially eliminates extraneous Out-Of-Plane acoustic noise. One embodiment includes a multiple channel multiplexing system for monitoring insect treatment processes in structures such as homes and other buildings. The real time data is used to determine the effectiveness of treatments as well as the time required to produce an effective treatment for termite eradication.

7 Claims, 23 Drawing Sheets

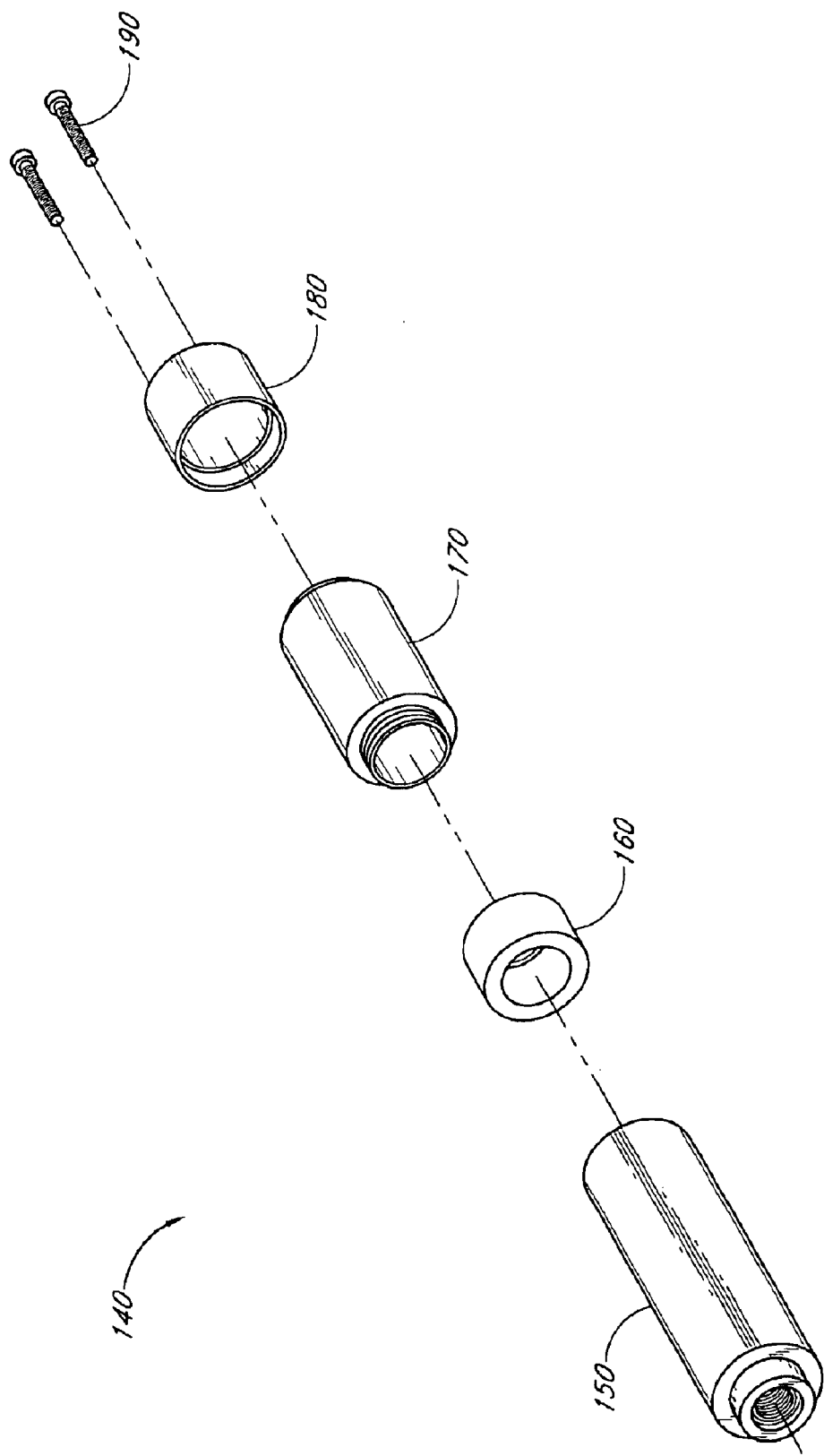

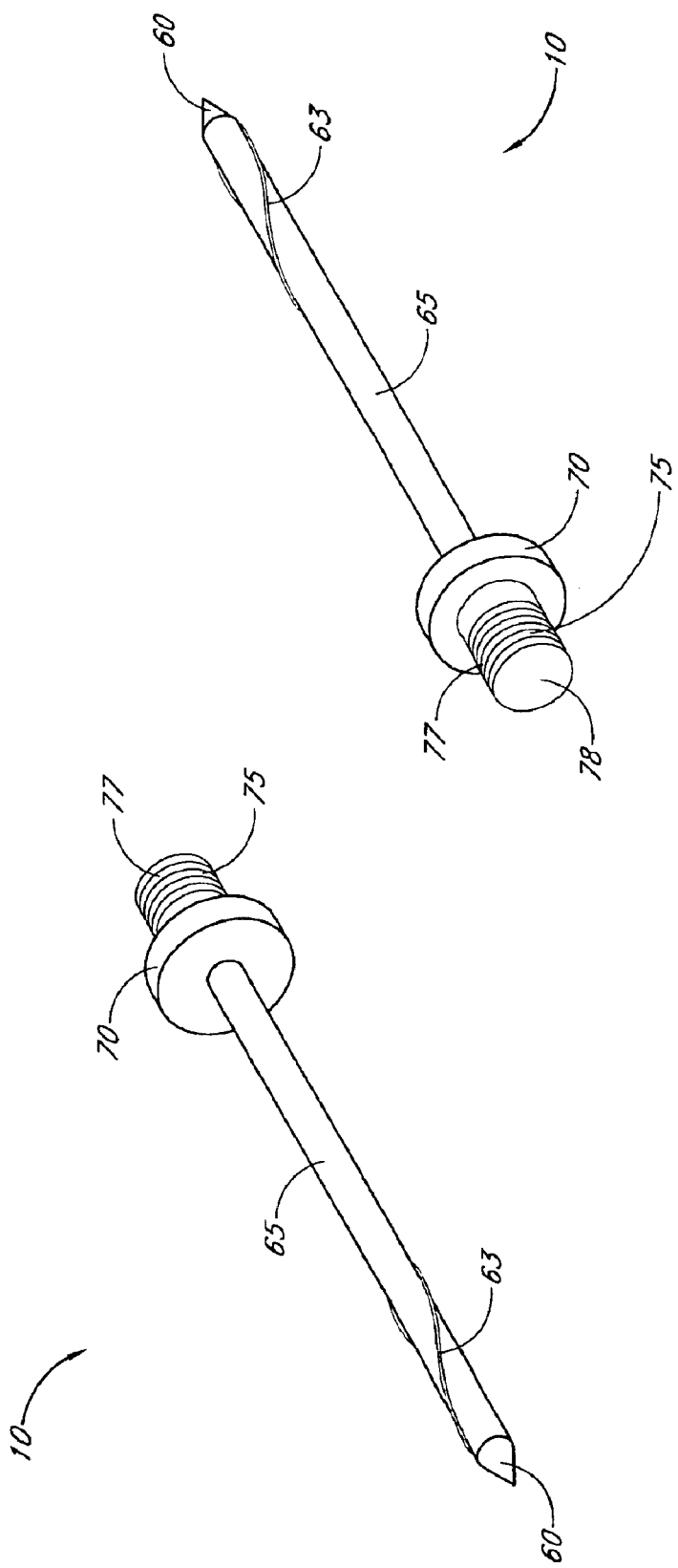

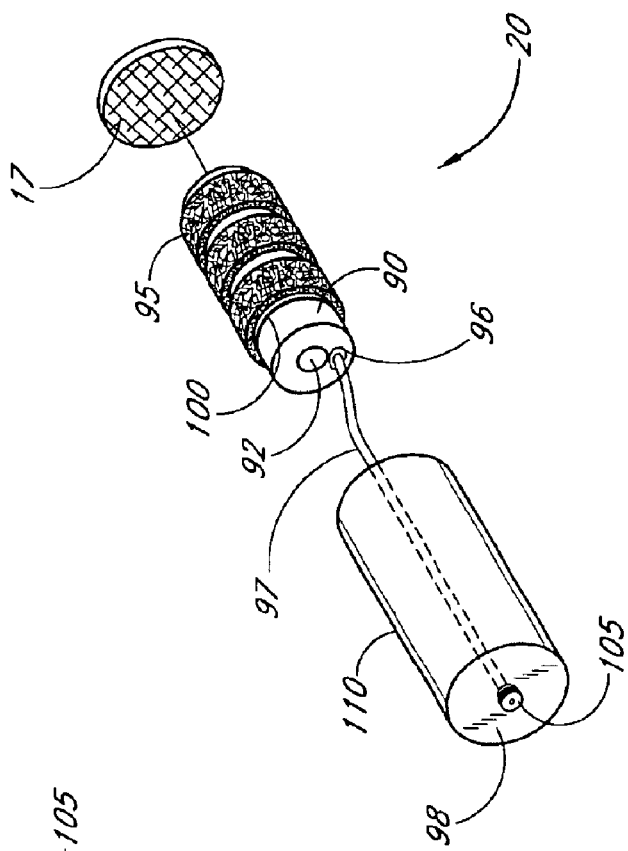
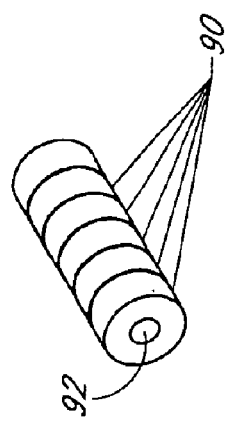
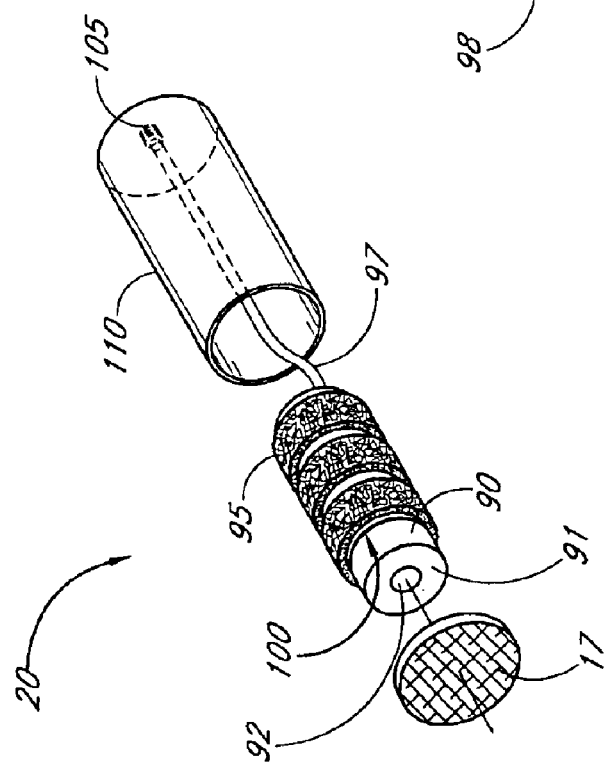

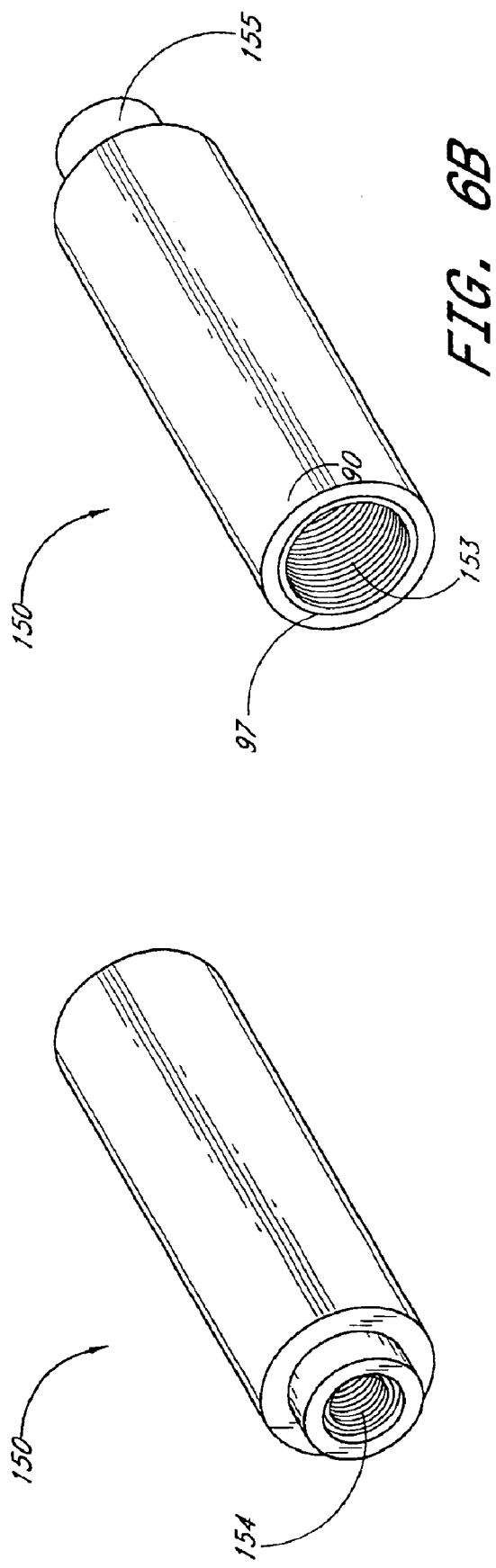
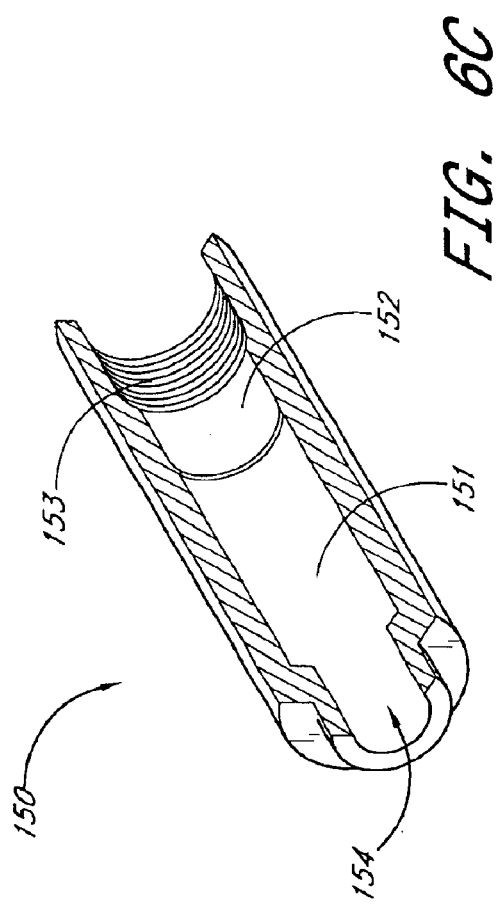
FIG. 6B
FIG. 6C
FIG. 6A

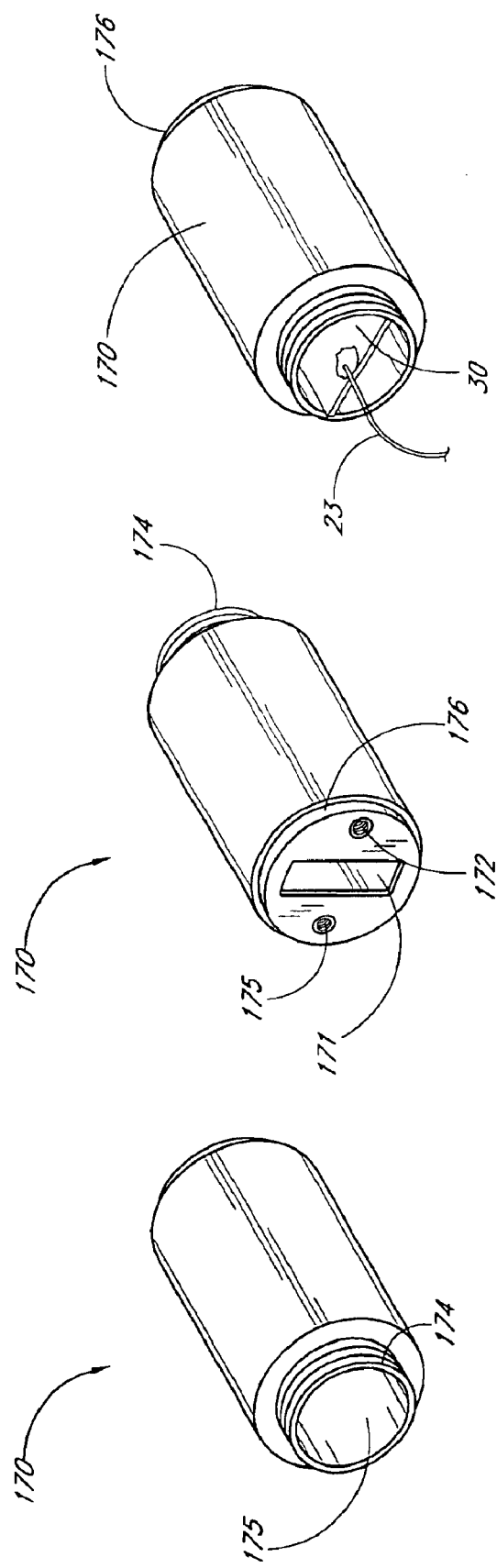

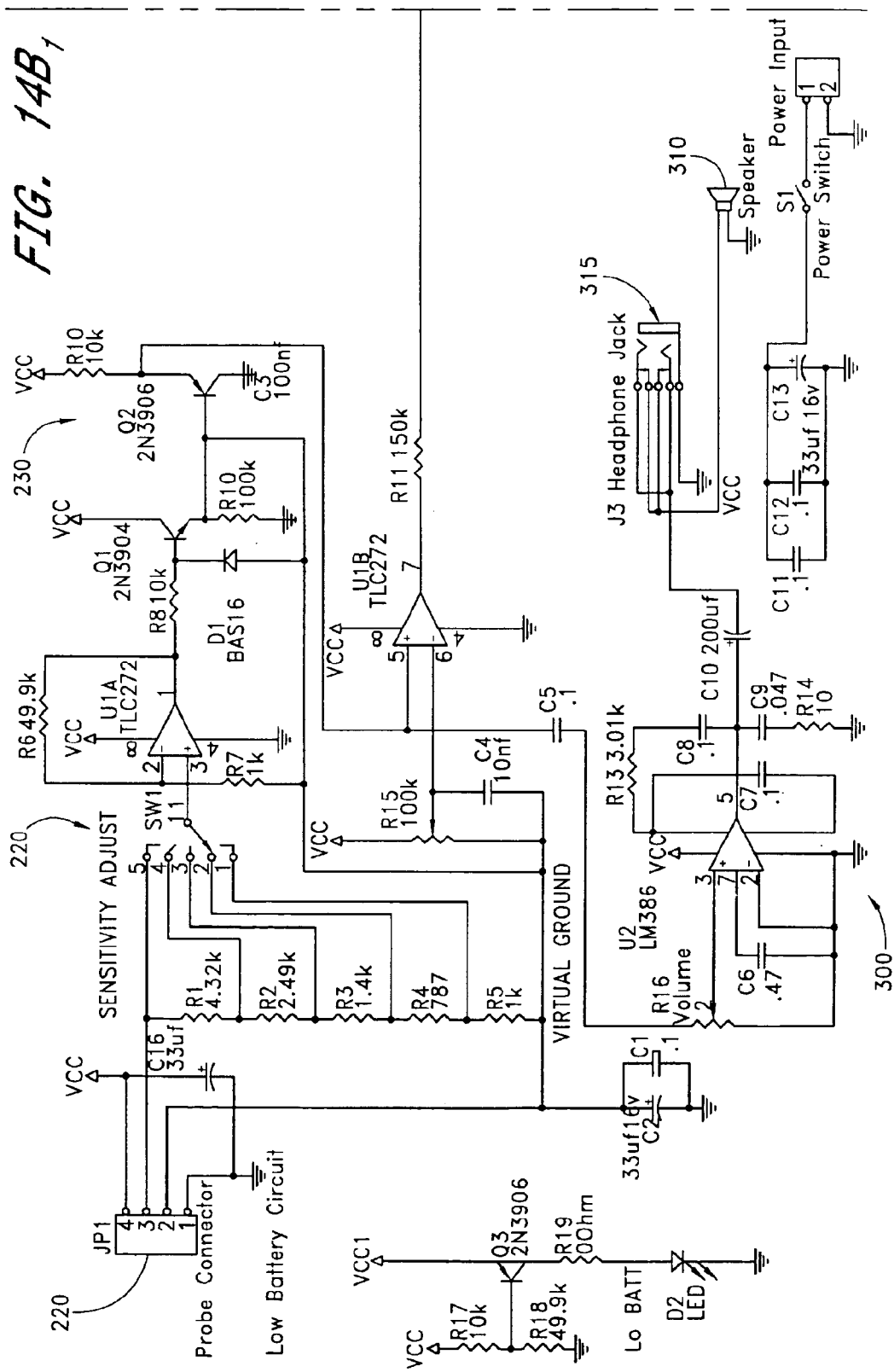

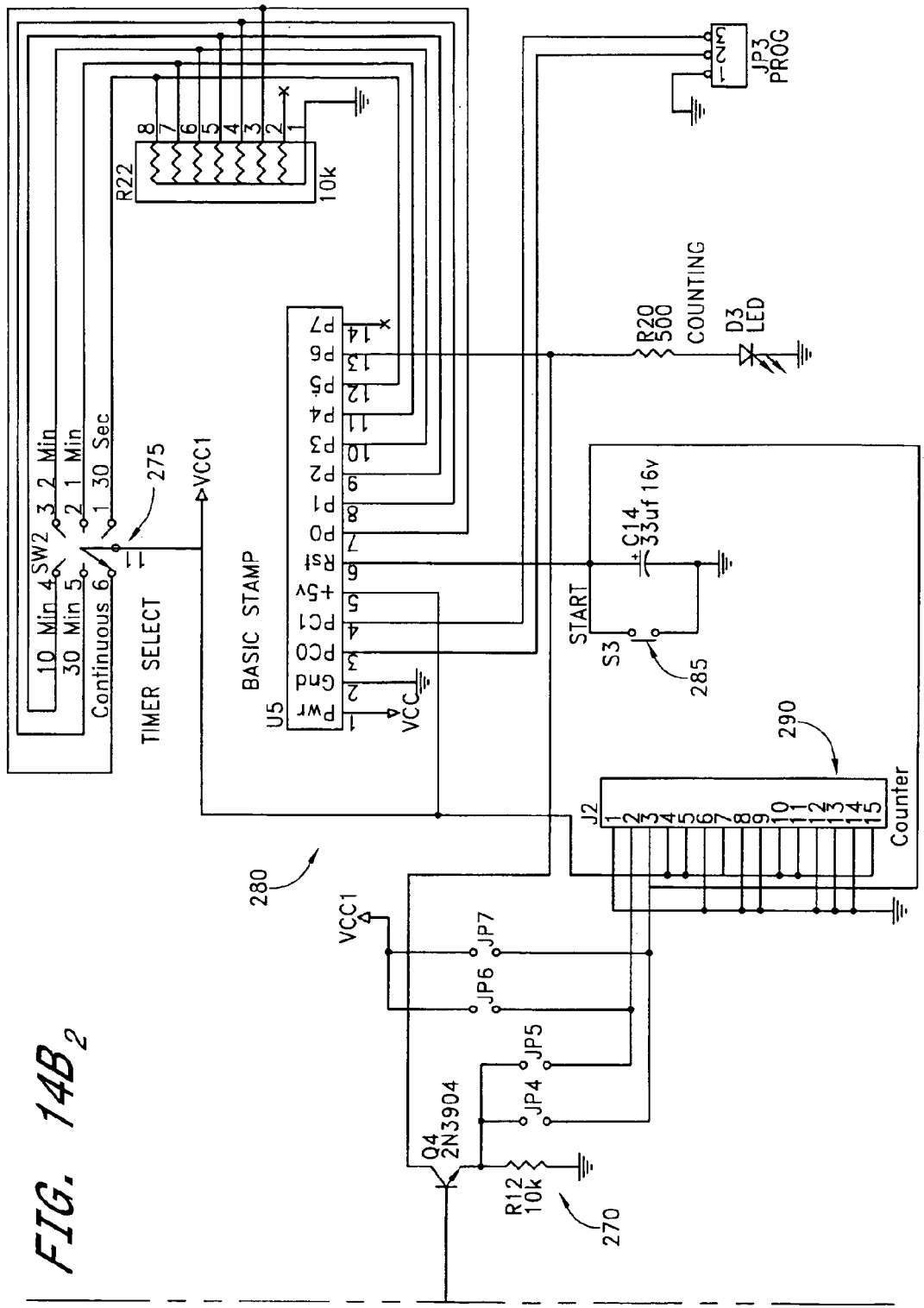
FIG. 14B₂

FIG. 18

| Run Time | minutes | events | HF amp | LF amp | ratio | ratio filter set at 2 |
|---|---|---|---|---|---|---|
| 23.85 | 0.3975 | 130 | 298 | 83 | 3.59 | FILTER ON |
| 23.9 | 0.398333 | 131 | 840 | 322 | 2.61 | TERMITES |
| 24.01 | 0.400167 | 132 | 1519 | 576 | 2.64 | |
| 24.12 | 0.402 | 133 | 415 | 117 | 3.54 | |
| 24.17 | 0.402833 | 134 | 728 | 156 | 4.66 | |
| 24.34 | 0.405667 | 135 | 391 | 181 | 2.16 | |
| 24.45 | 0.4075 | 136 | 322 | 88 | 3.67 | |
| 24.61 | 0.410167 | 137 | 439 | 166 | 2.65 | |
| 24.67 | 0.411167 | 138 | 1133 | 425 | 2.67 | |
| 24.83 | 0.413833 | 139 | 298 | 127 | 2.35 | |
| 24.89 | 0.414833 | 140 | 288 | 98 | 2.95 | |
| 25.05 | 0.4175 | 141 | 425 | 137 | 3.11 | |
| 25.16 | 0.419333 | 142 | 532 | 225 | 2.37 | |
| 25.43 | 0.423833 | 143 | 322 | 142 | 2.28 | |
| 25.49 | 0.424833 | 144 | 791 | 322 | 2.45 | |
| 25.54 | 0.425667 | 145 | 640 | 635 | 1.01 | FILTER OFF |
| 25.6 | 0.426667 | 146 | 5615 | 5327 | 1.05 | RUBBING BOARD |
| 25.65 | 0.4275 | 147 | 6367 | 6055 | 1.05 | |
| 25.65 | 0.4275 | 148 | 5625 | 4902 | 1.15 | |
| 25.71 | 0.4285 | 149 | 6221 | 6030 | 1.03 | |
| 25.76 | 0.429333 | 150 | 3276 | 3940 | 0.83 | |
| 25.76 | 0.429333 | 151 | 1948 | 2427 | 0.8 | |
| 25.82 | 0.430333 | 152 | 454 | 322 | 1.41 | |
| 25.87 | 0.431167 | 153 | 3125 | 3066 | 1.02 | |
| 25.87 | 0.431167 | 154 | 2822 | 2671 | 1.06 | |
| 25.93 | 0.432167 | 155 | 3135 | 3936 | 0.8 | |
| 26.04 | 0.434 | 156 | 376 | 259 | 1.45 | |
| 26.04 | 0.434 | 157 | 1279 | 1392 | 0.92 | |
| 26.09 | 0.434833 | 158 | 996 | 908 | 1.1 | |

DETECTION OF MOVEMENT OF TERMITES IN WOOD BY ACOUSTIC EMISSION TECHNIQUES

PRIORITY CLAIM

This application is a continuation of U.S. application Ser. No. 10/189,283, filed Jul. 1, 2002 now abandoned entitled "Detection of Termites in Wood By Acoustic Emission Techniques", entire content of which is hereby expressly incorporated by reference, which claims the benefit of U.S. Provisional Application No. 60/302,419 filed Jun. 29, 2001 entitled "Detection of Termites in Wood by Acoustic Emission Techniques," and U.S. Provisional Application No. 60/316,721 filed Aug. 30, 2001 entitled "Elimination of Extraneous Noise Sources from Acoustic Emission Based Termite Detection Instrument By Use of Modal Ratios."

FIELD OF THE INVENTION

This invention relates to insect detection by using acoustic emission technology. More particularly, the invention uses acoustic emission tools to detect the ultrasonic signals generated by wood-boring or wood-feeding insects as they feed or move within wooden objects.

BACKGROUND OF THE INVENTION

Wood-boring and wood-feeding insects, most notably termites, damage and destroy real property and natural resources in the United States every year. Although the extent of the harm shows regional disparity, the annual, direct cost attributable to these creatures across the nation is measured in the billions of dollars. Indeed, the United States Department of Agriculture estimates that the damage caused by the Formosa Subterranean Termite alone exceeds one billion dollars annually.

If the wood-destroying insects are detected, various extermination methods are demonstrably effective at curing the infestation problem which prevents further damage. Chemical and thermal treatments of infested wooden objects, for example, produce positive results as extermination techniques. However, timely insect detection itself has emerged as the better part of the challenge to mitigating termite damage.

The most common method in use today to detect termites is visual inspection. Observables such as surface ridges corresponding to internal termite tunnels, or termite waste (sawdust) may be evident at or near the infested areas. In extreme cases, the integrity of a wooden object may be compromised, or structural failure has already occurred.

As conclusive as visual evidence may be, the problems with the visual inspection technique are manifold. First, the test's subjective nature promotes inconsistent results that are neither reproducible nor lend themselves to error analysis. Second, and particularly important in the context of habitable structures, situations may exist where the infested area is not readily accessible, or where visual inspection is otherwise hampered by wallboard, plaster, insulation and the like. And third, by the time the infestation indicators are prominent enough to warrant attention, the lion's share of the damage may have occurred.

One line of inquiry has focused on the sonic signatures generated by insects in infested sites. This method monitors the human-audible portion of the spectrum (20 Hz to 20,000 Hz) to detect insects feeding on an agricultural sample of interest. However, this method suffers from a low signal-to-noise ratio since the audible portion of the spectrum necessarily records high levels of background unrelated to the insects' activities.

Another line of inquiry has been Acoustic Emission. "Acoustic Emission" (AE) may be defined as the release of elastic energy by a material as that material undergoes deformation. The deformation induces In-Plane (IP) and Out-Of-Plane (OOP) waves by causing mechanical disturbances within the material at points of inhomogeneity. For example, AE is widely employed as a non-destructive technique to detect cracks in metal parts and plate-like metal structures. To test the material, a static stress is applied to the part or plate under scrutiny. The applied stress causes the cracks, if any, to be fractionally extended. The extension of the cracks liberates energy at the leading edges of the cracks, and the energy propagates through the material as mechanical waves.

Advances in AE technologies, particularly the construction of transducers having peak sensitivity at ultrasonic frequencies, facilitated the development of the first-generation, AE-based termite detector.

These devices converted the OOP mechanical wave caused by termites tearing the wood during feeding into electrical signals later manipulated electronically. However, the accuracy of all devices based on AE have been unsatisfactory and, for the reasons described below, AE based devices suffer from most of the same drawbacks as their sonic progenitors, as well as the inadequacies of the visual inspection method. First, the devices were only capable of detecting the stress waves produced by feeding termites. Stress waves caused by termites feeding are the highest amplitude stress waves produced by an active colony; thus greater sensitivity is required to detect other forms of termite activity such as their movement within an infested object.

Second, the sensitivity of the first generation termite detectors is low. Independent studies testing the sensitivity of the instruments found that the devices, placed 50 cm from a feeding termite colony, only detected the activity about half the time. Furthermore, even in those tests where the detector was placed in close proximity to the activity, the recorded count rate was only between five and twenty five counts per minute. Therefore, background events remain a concern even though the background is reduced in the ultrasonic frequency range.

Third, the first-generation termite detectors are sensitive to the (OOP) waves alone. The transducer is placed in direct contact with the surface of the wood and will detect only the OOP waves, traveling across the grain of the wood rather than the IP waves traveling along the grain of the wood. As a consequence of preferentially detecting the OOP waves, the signal strength (and by corollary the instrument's sensitivity) is less than optimal because the attenuation of stress waves propagating across the grain of the wood to produce an (OOP) displacement at the surface of the wood, is much greater than the attenuation for stress waves propagating along the grain of the wood (IP).

Finally, because the devices require the transducer to be in contact with the surface of the material under scrutiny, the first-generation instruments are limited in a manner analogous to the limitations of the visual inspection technique. Specifically, tests on most areas within habitable structures are hampered by difficulties of access, or by barriers to surface contact such as drywall and the like.

SUMMARY OF THE INVENTION

This invention provides improvements in apparatus and methods of ement of wood-boring and wood-feeding insects in wood, particularly difficult to view or is blocked from direct contact.

Improved probe designs incorporating new elements minimize damage to the object of interest and its surroundings and enable the testing and measurement of wood that is difficult to access, or wood that is otherwise obstructed from direct contact.

One aspect of the present invention is improved sensitivity and access using a threaded wave guide that allows the probe to be screwed into virtually any wooden object. Securing the probe to the wood in this way enables the probe to make good mechanical contact with the wood, and to access the less-attenuated IP waves propagating along the grain of the wood. As a result, invention detects not only the high amplitude waves generated by feeding insects but also the lower amplitude waves caused by the movement of insects within the wood. This advance over the art improves the detection reliability (which is a function of sensitivity) and is also a factor in improving the position sensitivity of the device for localizing infestation.

In addition, the use of the threaded wave guide greatly enhances access to the wooden frames of habitable structures that are normally difficult to view, or are blocked from direct contact. This invention merely requires drill holes to be made through the surface barrier (such as wallboard) and into the wood to provide a detection environment identical with that of testing exposed wood. While not completely non destructive, this technique dramatically reduces damage to the object and its surroundings relative to the prior art devices requiring surface contact because, in the latter, the surface barriers must be taken down to enable direct contact between the transducer and the wood. For essentially the same reasons, the drill-hole access method is simpler and less time consuming than methods requiring surface contact.

One embodiment of the signal processing circuit includes an input stage that is a charge converter that outputs a voltage proportional to the input charge.

Another embodiment of the signal processing circuit includes an output stage using an operational amplifier with a small amount of positive feedback which function as a comparator with hysterisis rather than as a typical amplifier.

An aspect of one embodiment of the invention is in filtering the probe signal to improve the sensitivity of insect detection.

Another aspect of this invention is a multiple channel system providing a plurality of transducers located in a house or other building being treated for termites. The signals from the multiple channels enable determining the effectiveness and time of the treatment for termite eradication.

BRIEF DESCRIPTION OF THE DRAWINGS

FIG. 3 shows an exploded view of the probe housing;

FIG. 4(A) is a perspective view of the waveguide from a point substantially upstream of the waveguide;

FIG. 4(B) is a perspective view of the waveguide from a point substantially downstream of the waveguide.

FIG. 5(A) is an exploded view of the transducer viewed from the upstream side;

FIG. 5(B) is an exploded view of the transducer from the downstream side;

FIG. 5(C) is a perspective showing the series of cylinder crystals used to form the piezoelectric transducers;

FIG. 6(A) is a perspective view of the receptacle housing from a point substantially upstream;

FIG. 6(B) is a perspective view of the receptacle housing from a point substantially downstream;

FIG. 6(C) is a cut away perspective view of FIG. 6(A).

FIG. 8(A) is a perspective view of the preamplifier housing from a point substantially upstream;

FIG. 8(B) is a perspective view of the preamplifier housing from a point substantially downstream;

FIG. 8(C) is a perspective view of the preamplifier housing view of FIG. 8(A) with the preamplifier circuit board contained within the housing;

FIG. 14B is an electrical schematic of the other stages shown in FIG. 13;

FIG. 18 illustrates a representative excel sheet output from the system of FIG. 17.

DETAILED DESCRIPTION OF THE PREFERRED EMBODIMENT

The following description and examples illustrate in detail preferred embodiments of the detector system and method disclosed in the context of use to detect termites. The principles of the present invention, however, are not limited to the detection of termites. It will be understood by those of skill in the art in view of the present disclosure that the detector described may be applied to detect other types of wood-boring or wood-feeding creatures. One skilled in the art may also find additional applications for the devices and systems disclosed herein. Thus, the illustration and description of the detector and detection method in connection with termites are merely exemplary of one possible application of the detector and detection system.

The description below includes by way of specific example many specific components, dimensions and materials. However, it will be apparent to those knowledgeable in the art that other components, dimensions and materials may be used in other embodiments.

The Probe

The apparatus includes a probe 8 and signal processing electronics attached to the probe. To assist in the description of the probe and its components, "downstream" refers to the direction from the probe's conical tip 60 toward the probe's endcap 180 and "upstream" refers to the direction from the probe's endcap 180 toward the conical tip 60 of the waveguide 10.

Figure 1:
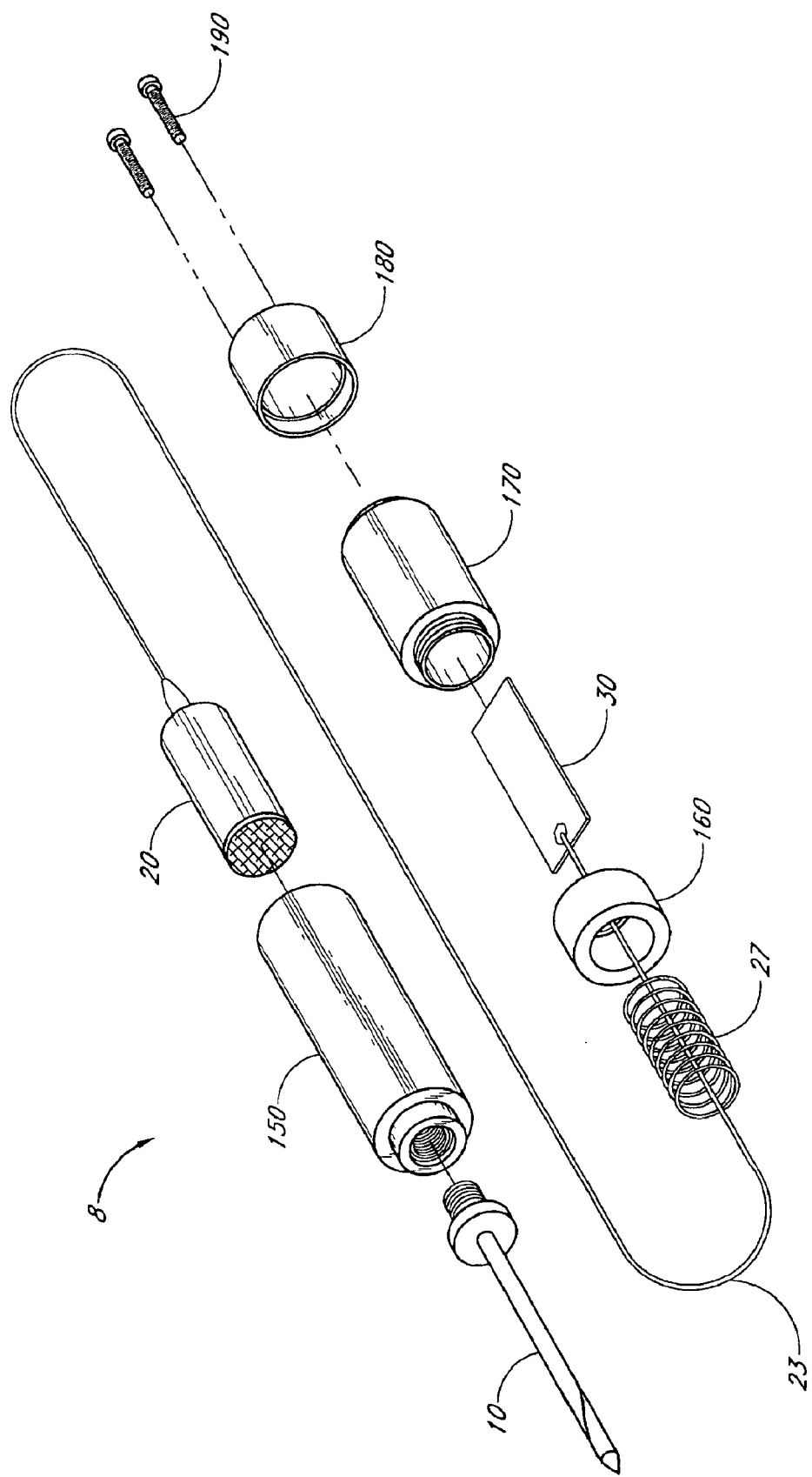
FIG. 1 shows a partially exploded view of the probe portion of the apparatus.

The probe 10 portion of the termite detector is shown in FIGS. 1 through 11. Referring to FIG. 1 the probe includes a waveguide 10, an acoustic couplant (not shown); a transducer 20, a spring 27; an insulated, coaxial wire 23; and a preamplifier 30. The probe housing shown in FIG. 3 includes an insert 160, a receptacle 150, a preamplifier housing 170, an endcap 180, and screws 190.

One advantageous way of making probe 10 is to machine it from a single solid piece of stainless steel.

Referring to FIG. 4, the waveguide 10 includes a conical tip 60; a first cylindrical, rod-like segment 65; a second cylindrical, disk-like segment 70; and a third cylindrical segment 75.

The first cylindrical segment 65 is the rod-like portion of the waveguide. This segment is not shrouded by the receptacle portion 150 of the plastic housing 140 (see FIG. 10). In one embodiment, the first cylindrical segment 65 is one-eighth of an inch in diameter with threads 63 over at least a portion of its length above the conical tip 60. In one embodiment, the threads are 6-1×½inch long which enables less time and fewer rotations to screw the probe into the wooden object. However, this particular choice of threading is purely for the convenience of the operator. Some form of threading is generally advantageous because the threads ensure good mechanical contact between the waveguide 10 (threads 63 and conical tip 60) and the wooden object.

The conical tip segment 60 also makes contact with the wooden object when the waveguide is tightened into the object. In one embodiment, the opening angle of the sharp-point cone 60 is forty degrees. The conical shape helps to refract mechanical waves into the waveguide 10 and hence improves the sensitivity of the instrument.

The third cylindrical segment 75 is the portion of the waveguide 10 that attaches to the plastic housing 140 (see also FIG. 11), and makes contact with the transducer 20. This segment includes threads 77 to provide a secure connection with the tapped receptacle 150 portion of the housing 140. In one embodiment the third cylindrical segment 75 has a diameter of 0.375 inches, a length of 0.33 inches and is threaded [6-32]. The polished planar face 78 at one extreme of the waveguide 10 makes contact with the ceramic shoe 17 (see FIG. 2) of the transducer 20 when the waveguide 10 is tightened into the receptacle portion 150 plastic housing 140 and the probe is fully assembled. The separability of the transducer 20 and waveguide 10 enables the user to clean, repair, or replace the components independently.

The second cylindrical, disk-like segment 70 is an upstream plug for the receptacle portion 150 of the plastic housing 140. In one embodiment this second cylindrical segment 70 is 0.125 inches long and has a diameter of one-half inch. This portion fits into the outermost, upstream volume of the receptacle portion 150 of the plastic housing 140 and is approximately flush with the housing 140 when the waveguide 10 is tightened into it (see also FIG. 10).

Figure 12:
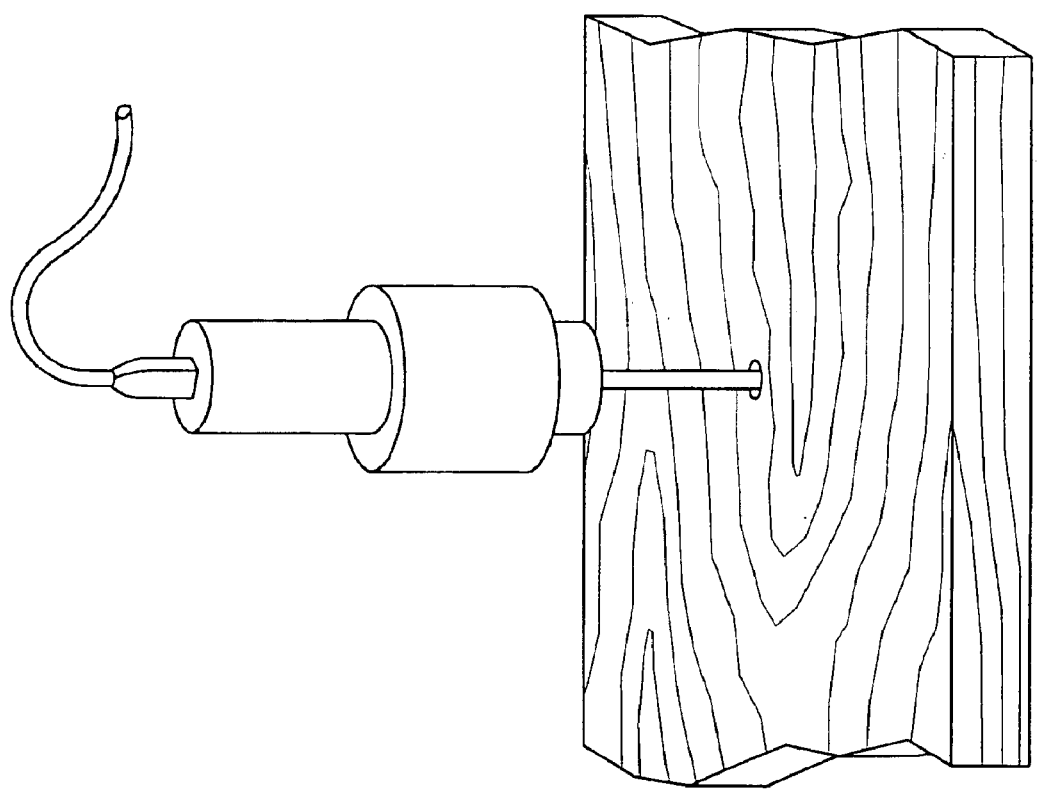
FIG. 12 is a perspective view of the probe waveguide inserted into a drill hole within a board being tested for termite inspection.

FIG. 12 shows the probe 8 in use wherein a hole is bored into the wood using a bit approximately the diameter of segment 65 and the waveguide 10 is screwed into this hole. The threaded waveguide 10, as opposed to mounting the transducer 20 on the surface of the wood, provides some significant advantages. First, wallboard or other surface barriers can be penetrated to allow the waveguide 10 to make contact with the underlying wood. Second, tightening the threaded waveguide 10 to mechanically couple it with the wood provides access to the extensional, IP stress waves traveling along the grain of the wood. This improvement alone increases the detector's sensitivity twofold because IP stress waves are not attenuated as much as OOP stress waves. Although the waveguide 10 is a significant feature of one embodiment of the invention, other embodiments are described below in which the transducer 20 is mounted directly to the wood under test.

A detailed drawing of the probe's transducer component is shown in FIGS. 5A, 5B and 5C. In one embodiment, the transducer 20 is a piezoelectric device having its peak sensitivity at a frequency of 40 Khz. Operation of the transducer at this frequency is high enough to eliminate the low frequency background noise, and is low enough to minimize wave attenuation in wood. The magnitude of the transducer's peak sensitivity is approximately one volt per nanometer of displacement. The transducer is advantageously calibrated in the displacement mode using a calibration that is traceable to the National Institute of Standards and Technology.

One embodiment of the transducer 20 includes cylindrical piezoelectric crystals 90, silver epoxy 100, a ceramic disk 17, cork liners 95, an electrical connector 105, and a stainless steel casing 110. These piezoelectric crystals 90 are commercially available from many vendors. The crystals 90 are right cylindrical with one-half inch diameter faces and one-quarter inch thickness. The modification to the crystals is that they are drilled through normal to their planar faces 92. The resultant hole 92 in each crystal 90 has a diameter of 0.180 inch. The diameter of the hole 92 in the crystals 90 is one of the parameters that defines the frequency at which the transducer 20 exhibits its peak sensitivity.

The piezoelectric crystals 90 are polarized along the cylindrical axis. In one embodiment, six crystals are stacked and glued together using the silver epoxy with the positive pole face of one crystal adjacent to the negative pole face of the next crystal. This results in a three-inch long, one-half inch diameter, cylindrical sensor with an 0.180 inch diameter, coaxial hole 92 through it. Conductivity along the common axis is achieved by depositing a thin layer of silver epoxy 100 between the adjacent crystals. The silver epoxy 100 also secures the crystals to each other to preserve the coaxial geometry.

The curved exterior surfaces of the crystals are protected by a cork liners 95 which substantially cover the length of the six-crystal stack. The cork liners 95 also provide an impedance mismatch to prevent the radial motion of the crystals 90 from being damped. This is advantageous because the radial motion cross-couples with the longitudinal (extensional) crystal motion to increase the amplitude of the throughput signal. The cork liners 95 also serve to reduce ambient noise, to isolate the crystals 90 from the stainless steel housing 110, and to protect the crystals 90 against physical damage. The stainless steel housing 110 provides the electrical ground for the system and also serves to protect the functional parts of the transducer 20.

The open face of the crystal 91 closest to the waveguide 10 is secured to a ceramic shoe 17 using silver epoxy 100; and the ceramic shoe 17 is bonded about its circumference to the stainless steel case 110 [with silver epoxy]. This is the negative pole of the crystal stack. The ceramic shoe 17 is cylindrical and coaxial with the piezoelectric crystals 90. The ceramic shoe 17 provides electrical isolation for the transducer 20 from the waveguide 10.

The open face of the crystal 96 closest to the preamplifier 30 is soldered to one end of a conductor 97 of copper or other electrically conductive member to transport the electrical signal generated by the crystals 90. This is the positive pole of the crystal stack. The other end of the conductor 97 is attached to the interior side of an electrical connector 105 located on the stainless steel face 98 of the stainless steel casing 110. A coaxial cable 23 (see FIG. 20) attaches to the connector 105 on the exterior of the stainless steel face 98 of the stainless steel casing 110 to deliver the electrical signal to the preamplifier 30. The electrical signal flows from the crystal sensors 90 along the conductor 97 through the connector 105 in the stainless steel casing 110, along the coaxial cable 23, and into the preamplifier 30.

The polished end 78 of the waveguide 10 and the ceramic disk 17 end of the transducer 20 are coated with an acoustic couplant (not shown). The acoustic couplant ensures good transmission of the energy between the waveguide 10 and the transducer 20. In the preferred embodiment the acoustic couplant used is petroleum jelly; however, one skilled in the art will recognize that there are numerous substitutes for the petroleum jelly in this context.

Figure 2:
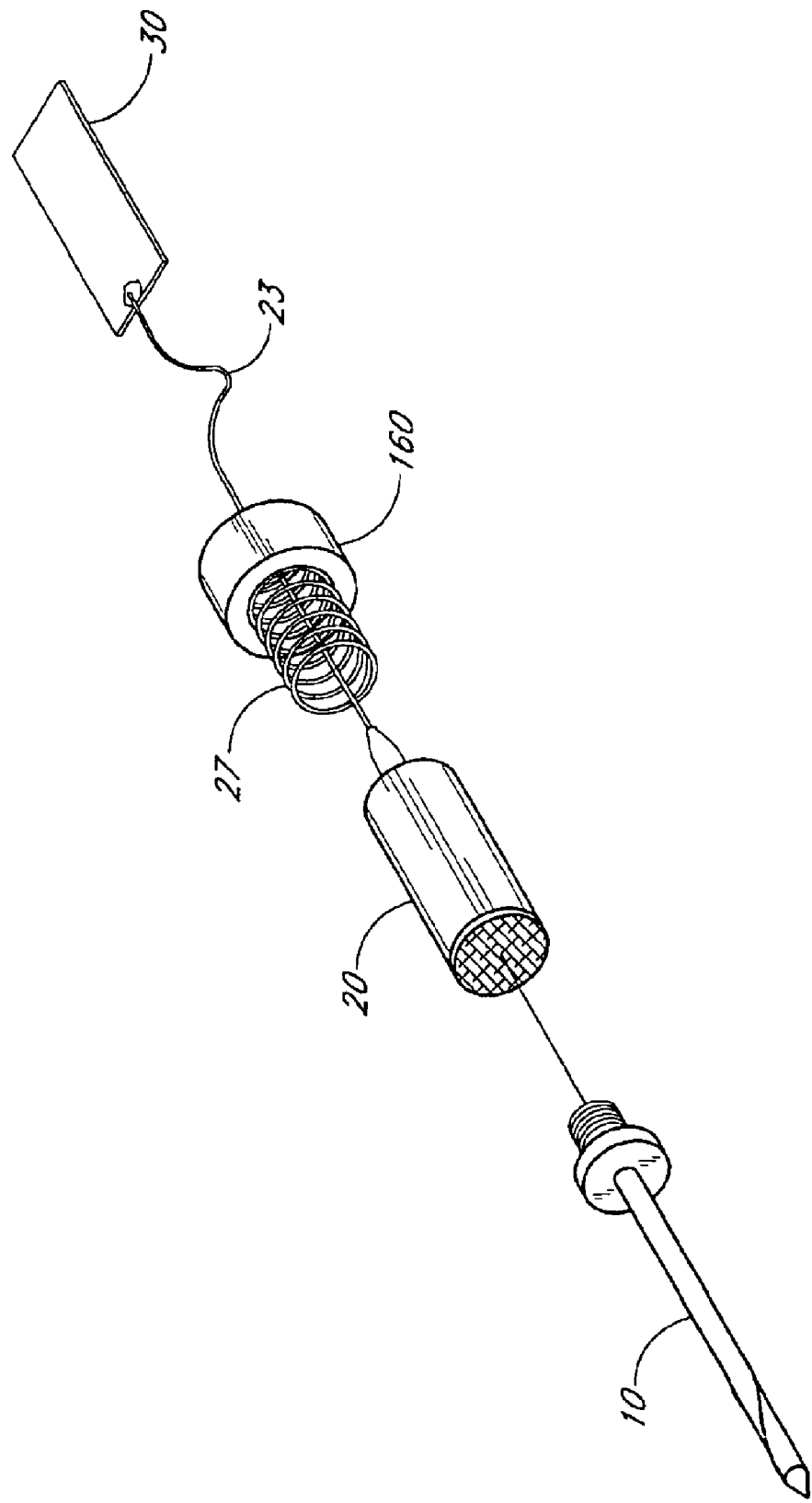
FIG. 2 shows an exploded view of the probe's components where the outermost housing components have been removed.
Figure 11:
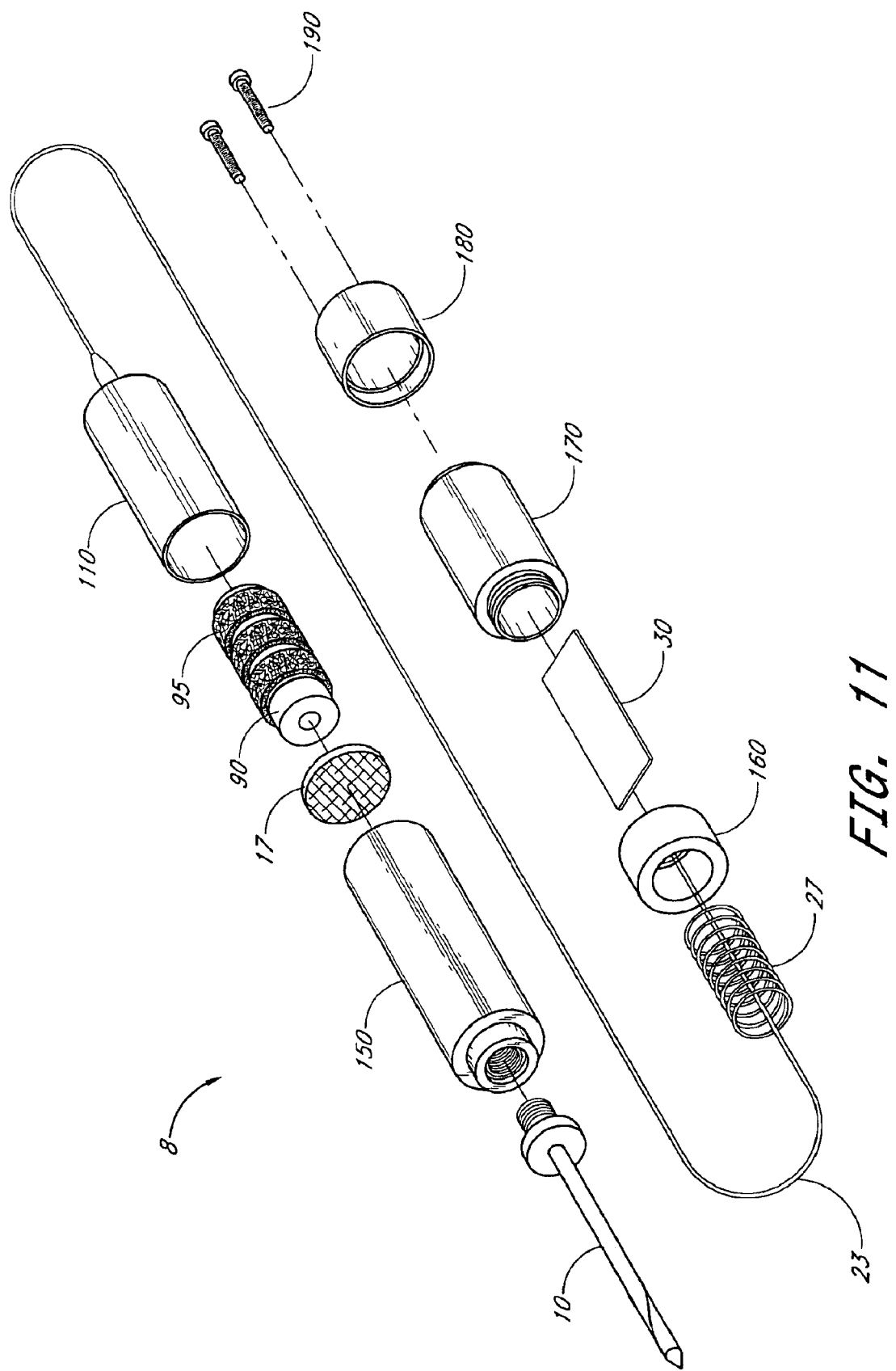
FIG. 11 is an exploded view of the probe portion of the apparatus.

The transducer 20 is spring loaded 27 within the plastic housing 140 (see e.g. FIGS. 1, 2, and 11. One embodiment of spring 27 provides ten pounds compression, is one inch long, without pressure, and has a helical radius of 0.3 inches. The spring 27 makes contact at one end with the stainless steel end 98 of the transducer casing 110, and at the other end the spring makes contact with the 'insert' portion 160 of the plastic housing 140. When the probe is assembled, the spring 27 is compressed and the pressure forces the ceramic disk 17 end of the transducer 20 into close contact with the polished end 78 of the waveguide 10. This pressure ensures good contact between the transducer 20 and waveguide 10 elements which results in higher signal strength. The pressure also stabilizes the transducer 20 so that it doesn't shift or lose contact with the waveguide 10 during the measurements. The helical radius of the spring 27 is sufficient to allow the coaxial cable 23 between the electrical connector 105 on the transducer 20 and the preamplifier 30 to pass through the spring 27 unimpeded.

Figure 10:
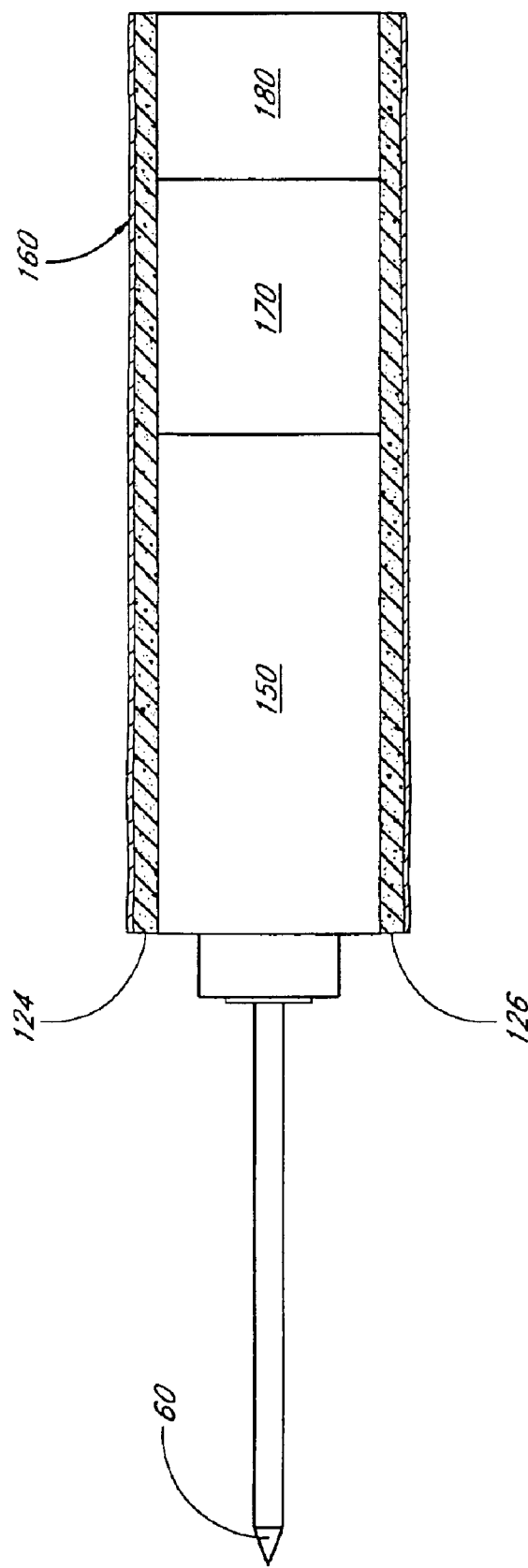
FIG. 10 is a side cross-sectional view of the fully assembled probe showing the sound absorbing elastomer and heat-shrink covers.

The curved portion of the probe's housing is wrapped in a sound absorbing elastomer 124 (see FIG. 10) which is held in place by heat-shrink tubing (see FIG. 10). The sound absorbing elastomer 124 functions as an attenuator for airborne signals that might otherwise be detected by the probe. This results in lower levels of background and thereby improves both the signal-to-noise ratio and the sensitivity of the probe. The sound absorbing elastomer 124 and the heat shrink tubing 126 are commercially available and well known to those skilled in the art. In addition to the above functions, the sound absorbing elastomer 124 and the heat-shrink tubing 126 serve to prevent users from inadvertently disconnecting the components of the housing 140.

Figure 13:
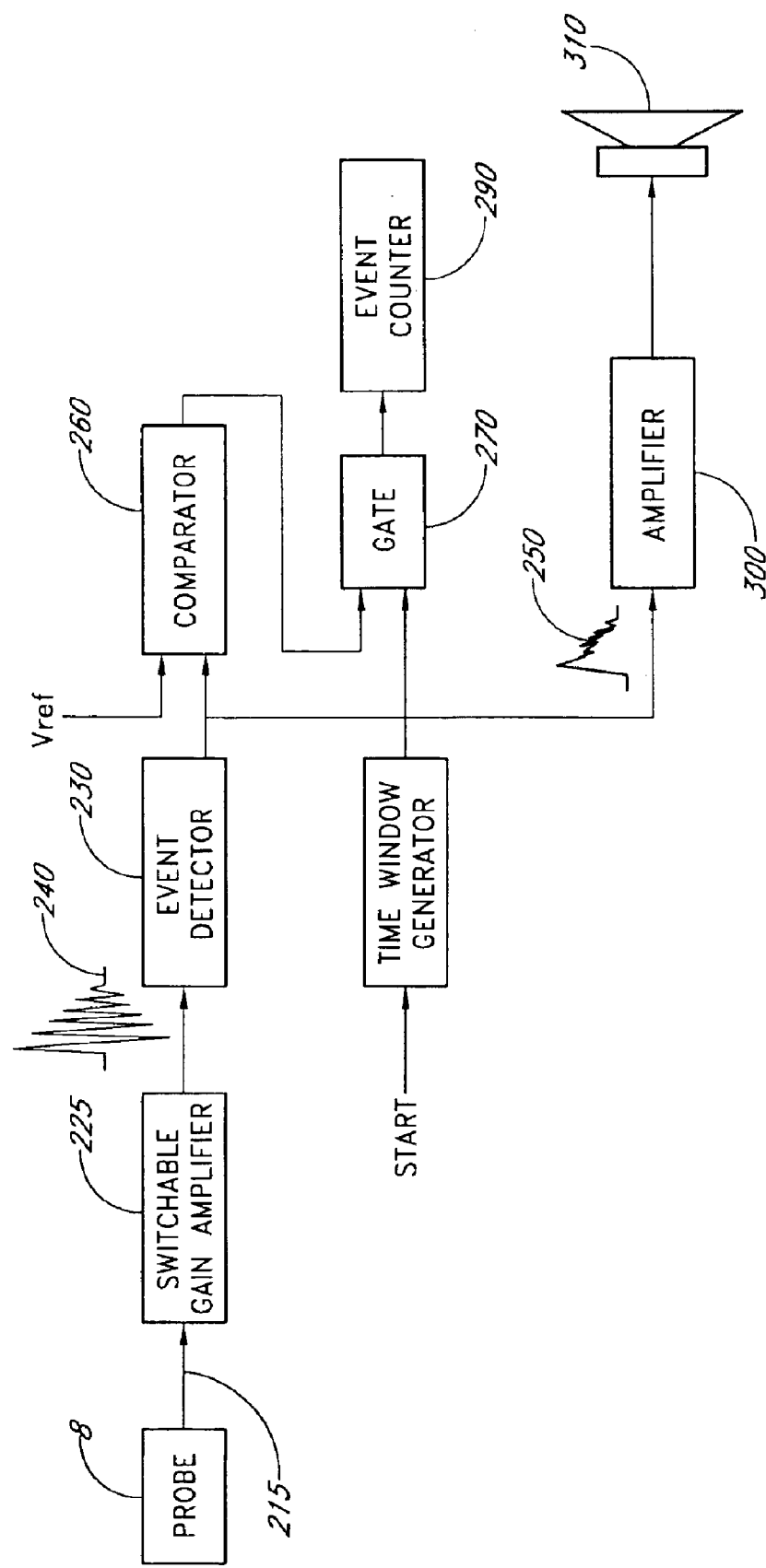
FIG. 13 is a block diagram of one embodiment of the probe and signal processing circuits.

A preamplifier 30 is also contained within the plastic housing 140 (see e.g. FIGS. 2, and 8(C)). A schematic diagram of one embodiment of the preamplifier circuit is shown in FIG. 13. In one embodiment, the preamplifier amplifies the transducer's electrical output by 60 dB. This translates into a final probe sensitivity of approximately 1.5 volts per picometer of displacement at 40 kHz.

The housing 140 is shown in FIG. 3. In one embodiment, the housing is constructed of Delrin®. Delrin® is a lightweight, high melting point polymer that is strong, stiff and abrasion resistant. Delrin® is used to house the essential elements of the probe to protect and preserve. One embodiment of the housing 140 is made up of five, separable components. The five separable components are: the receptacle 150, the insert 160, the preamplifier housing 170, the endcap 180, and the screws 190.

Figure 9B:
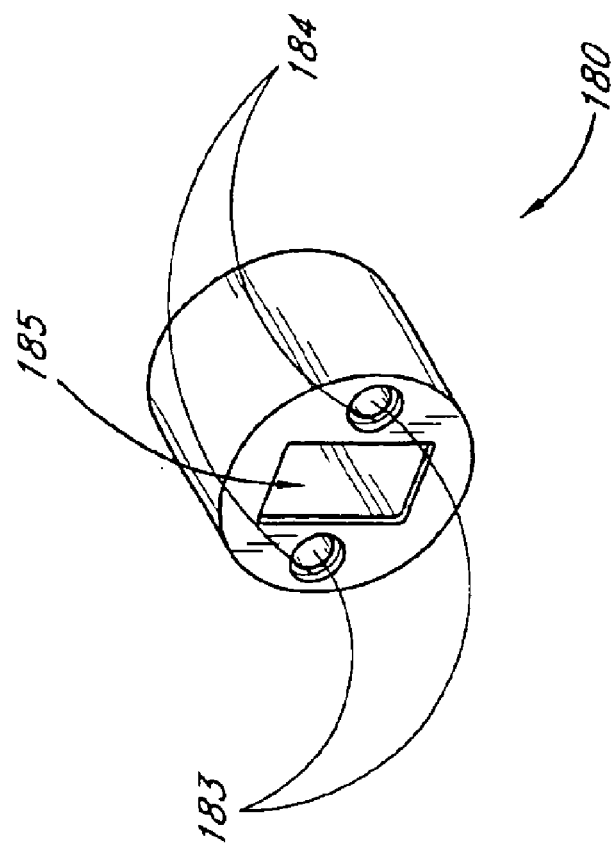
FIG. 9(B) is a perspective view of the endcap from a point substantially downstream.
Figure 9A:
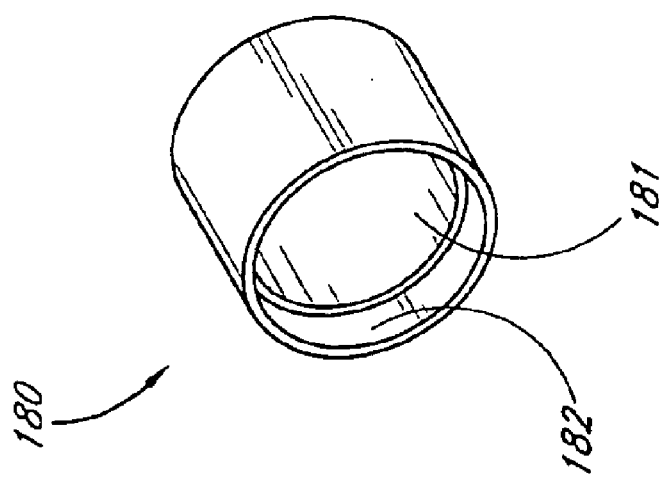
FIG. 9(A) is a perspective view of the endcap from a point substantially upstream.

The endcap 180 is shown in FIGS. 3 and 4, and it is the component of the housing 140 farthest from the waveguide 10 (not shown in FIG. 9, see FIG. 1. In one embodiment, the endcap 180 is machined from a solid, cylindrical piece of material having diameter 1.125 inches and length 0.875 inches. A first volume 181 is bored out of the cylinder having diameter 0.860 inches and to a depth of 0.770 inches. A second volume 182 is bored out having diameter 1.000 inches and to a depth of 0.180 inches. Both bore holes 181, 182 are coaxial with the cylindrical material and their depths are measured from the upstream face of the starting material.

The downstream face of the starting material is drilled through at two points 183 along the circumference of a 0.750 inch diameter bolt circle. Those two points 183, located at 180 degree relative spacing about the bolt circle, are drilled through to a diameter of 0.104 inches. The bolt circle is concentric with the cylindrical axis of the starting material. This same face is bored out 184 at the two points on the bolt circle described above to a depth of 0.075 inches and to a diameter of 0.218 inches. Also, an approximately rectangular section 185 is cut out of the same (downstream) face of the cylinder. The rectangular cut-out 185 is approximately 0.625 inches by 0.440 inches. The cut-out section 185 is oriented such that a line between the centers of the two drilled-through points 183 on the bolt circle would bisect the 0.625 inch lengths. The rectangular cut out 185 permits a standard, four conductor, RJ-11 telephone jack connector (not shown) to be placed into and fixed within the rectangular slot 185. The output signals from the preamplifier 30 are carried by suitable conductors to an RJ-11 jack 205 (see FIG. 13) which can then be releasably connected conductors (shown in FIG. 13) to an external processor.

The endcap 180 section slips over the ledge on the downstream side of the preamplifier housing 170 (see FIGS. 1 and 3). When the endcap 180 and preamplifier 170 housing are properly aligned, two screws 190 are passed through the endcap holes 183 and the two components are secured by tightening the screws 190 into the threaded 172 holes 173 of the preamplifier housing 170 (see FIG. 8).

Figure 7B:
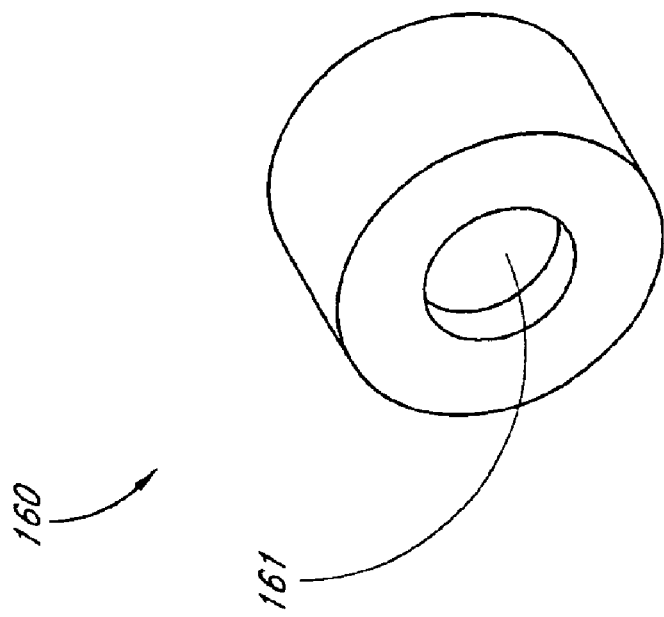
FIG. 7(B) is a perspective view of the insert portion of the housing from a point substantially downstream.
Figure 7A:
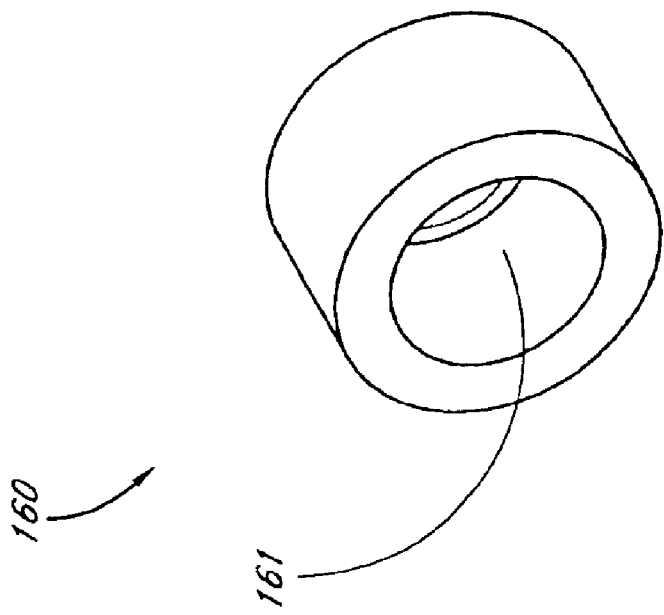
FIG. 7(A) is a perspective view of the insert from a point substantially upstream.

One embodiment of insert 160 shown in FIG. 7 is machined from a solid, cylindrical piece of material having diameter 0.810 inches and length 0.440 inches. The insert starting material is drilled through, leaving a hole 162 of diameter 0.375 inches in the cylindrical starting material. An additional, volume 161 is bored out of the (now tube-like) cylindrical starting material having diameter 0.500 inches and to a depth of 0.312 inches. Both the drill-through volume 162 and the bored out volume 161 are coaxial with the cylindrical starting material.

When the probe housing 140 is fully assembled, the insert 160 is completely contained within the receptacle portion 150 of the housing 140. The insert 160 fits into the identifiable volume 152 of the receptacle portion 150 in FIG. 6(C). The insert 160 provides a surface against which one end of the spring 27 exerts pressure (see FIG. 2). The other end of the spring 27 exerts pressure on the stainless steel face 98 of the stainless steel casing 110 of the transducer 20 so that the transducer 20 and waveguide 10 maintain good mechanical contact with each other. The coaxial cable 23 running between the transducer 20 and the preamplifier 30 passes through the insert 160 (see FIGS. 1, 2, 11).

One embodiment of the receptacle 150 is shown in FIGS. 1 and 2. The receptacle portion 150 of this housing 140 is made by machining a cylindrical piece of starting material having diameter 1.125 inches and length 3.5 inches. The cylinder is bored out to three different diameters and depths. The bored out volumes are coaxial with the cylindrical axis of the starting material and their depths are measured from the starting material's downstream cylindrical face. The first bore is at a diameter of 0.750 inches and extends to a depth of 3.000 inches. The second bore 152 is to a diameter of 0.815 inches and to a depth of 1.000 inches. The third bore 153 is to a depth of 0.445 inches and the diameter accommodates ⅞-16 threads. The third bore is tapped [threaded female] to a depth of at least 0.375 inches of the 0.445 inch total, and to a minimum thread relief of 0.07 inches. This tapped segment 152 connects with the ⅞-16 threaded male section 174 of the preamplifier housing 170 (see FIG. 8).

The remaining solid portion of the receptacle 150 starting material is drilled through 154 from the upstream cylindrical face and tapped for ⅜-16 threads. The through hole 154 is coaxial with the cylindrical starting material. The upstream face is bored out to a depth of 0.125 inches and to a diameter of 0.500 inches coaxial with the cylindrical starting material. The bored out region is further beveled at a forty-five degree angle an additional 0.030 inches into the material. Finally, the cylindrical surface, beginning at the upstream face, is lathed down to an outside diameter of 0.750 inches extending along 0.375 inches of the cylindrical length 155. The ⅜-16 tapped [threaded female] segment 154 connects with the ⅜-16 threaded male section 75 of the waveguide 10. The bored out region at the upstream end of the receptacle 154 allows for the waveguide's second, disk-like cylindrical segment 70 to insert into it such that the two are approximately flush when the waveguide 10 is tightened into the receptacle 150.

Another embodiment (not shown) further secures the waveguide 10 within the receptacle 150 using set screws. In that embodiment, the upstream, lathed portion of the receptacle is drilled through perpendicular to the cylindrical axis, and the through holes are tapped to accommodate the threading of set screws. After the waveguide 10 is tightened into the receptacle 150, the set screws are inserted into the tapped through holes and tightened until contact is made with the second, disk like, cylindrical portion 70 of the waveguide 10.

One embodiment of the preamplifier housing portion 170 shown in FIG. 8 is machined from a cylindrical starting material having diameter 1.125 inches and length of 2.375 inches. The cylinder is bored out 175, coaxial with the cylindrical starting material, from the upstream face to a depth of 2.000 inches and to a diameter of 0.750 inches. The downstream face of the starting material is drilled through at two points 173 along the circumference of a 0.750 inch diameter bolt circle. Those two points 173, located at 180 degree relative spacing about the bolt circle, are drilled through and tapped [threaded female] through for 4-40 threaded rod 172. The bolt circle is concentric with the cylindrical axis of the starting material. Also, a rectangular section 171 is cut out of the downstream face of the cylinder. The rectangular cut-out 171 is 0.760 inches by 0.250 inches. The cut out section 171 is oriented such that a line between the centers of the two drilled-through points 173 on the bolt circle would bisect the 0.760 inch lengths.

Both ends of the cylindrical starting material have a lathed length 174, 176. The upstream end is lathed and threaded to ⅞-16 rod 174 along the cylindrical length for 0.320 inches 174. This upstream end of the preamplifier housing 170 may then be screwed into the downstream end 153 of the receptacle 150 which is tapped for ⅞-16. The downstream end of the preamplifier housing 170 is lathed to a 0.999 inch diameter over 0.125 inches of the cylindrical length 176. This downstream end 176 of the preamplifier housing 170 fits into the upstream portion 182 of the endcap 180. When the endcap 180 and the preamplifier housing 170 are properly aligned, the two components are fastened together by passing 4-40 threaded screws 190 through the endcap through holes 183 and tightening them into the tapped holes 173 of the preamplifier housing 170.

Operation of the Probe

Figure 15A:
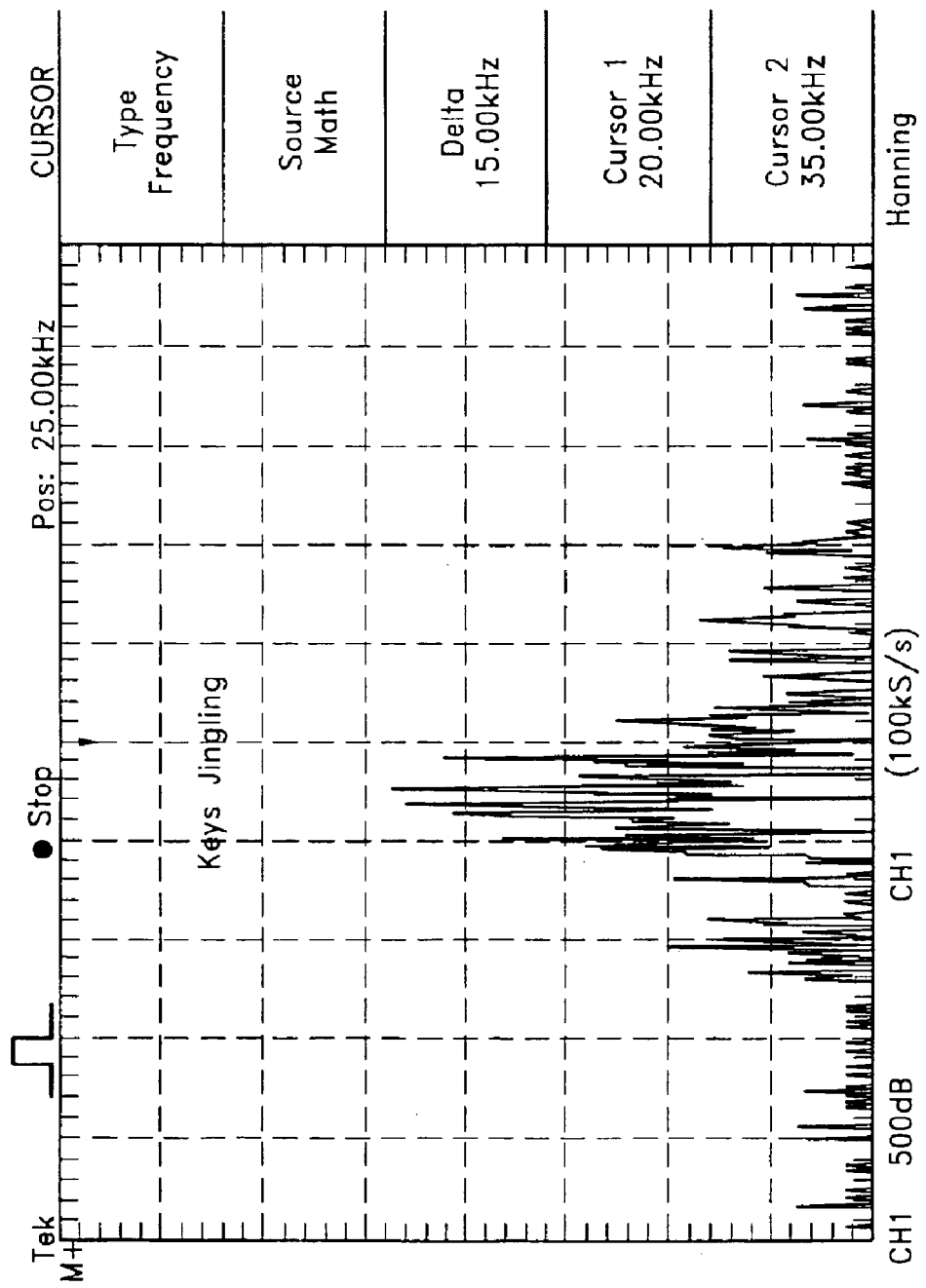
FIG. 15A graphically illustrates the output signals produced by the transducers from an extraneous noise source (keys jingling)

The transducer 20 coupled to waveguide 10 is inserted into a drill hole in wood. The probe 8 operates in the following manner. The waveguide 10 provides improved mechanical coupling to the wood and intersects the high frequency extensional and shear waves propagating along the grain of the wood. These in-plane stress waves are produced by feeding and movement of termites of their gallery. These higher frequency stress waves are more difficult to detect by a sensor mounted on the surface of the wood because more attenuation of the stress waves occurs across the grain than along the grain of the wood. For certain situations that do not allow a drill hole to be made, the transducer 20 can be coupled to the surface of the wood with petroleum jelly or other couplants. Representative output signals from probe 8 are illustrated in FIG. 15A.

Systems and Methods for Processing the Probe Output Signals

The overall block diagram of the system is shown in FIG. 12. The output signal of the probe 8 is typically an analog signal. Using the circuitry of one embodiment illustrated in FIGS. 12, 13 and 14, this analog signal is converted to a series of pulses. These pulses are then detected to determine insect infestation of the tested wood. In one embodiment, these pulses are detected both audibly and by counting the pulses over a preset time period.

Referring now to FIG. 13, the transducer sensor 20 is coupled to a series of pre-amplifier stages 200. The electrical connection between the transducer 20 and the input of the pre-amplifier stages 200 located on the printed circuit board is kept physically short by locating the stages 200 on a single printed circuit board 30 mounted in the housing 170 of the probe 8. The output of the pre-amplifier stages is connected to the RJ-11 jack 205.

The transducer 20, pre-amplifier circuit stages 200, and jack 205 are shown in FIG. 12 as probe 8. A suitable cord 215 attaches jack 205 to jack 220 of FIG. 14. The output of the pre-amplifier stages 200 is thereby connected to the input of a switchable gain amplifier 225. The amplified transducer signal is connected to an event detector 230. Referring to FIG. 14, event detector 230 includes NPN and PNP transistors, a capacitor and diode. The function of this current is to rectify and filter an alternating signal burst 240 from the transducer produced, for example, by insect activity, and produce a rectified pulse shown at 250. Signal 250 is input to comparator stage 260 wherein the amplitude of signal 260 is compared to the preset voltage reference Vref so that an output pulse is delivered to the input of gate 270 when the amplitude of 250 exceeds the voltage Vref.

Gate 270 is opened for a time interval selected by switch 275 (FIG. 2) of the time window generator 280. This open window is initiated by closing switch 285 (FIG. 14) during which time, the output pulses from the comparator 260 are counted by event counter 290.

An audible detection of the output of the event detector 230 is provided by audio amplifier stages 300 connected to a loudspeaker 310, ear phone jack 315 (FIG. 14) or similar audio output device.

Although the circuitry of the embodiment shown described converts the probe signal to a series of pulses above a preset threshold level, it will be apparent to those skilled in the art that a measurement of insect activity may be achieved in other ways. For example, the zero crossings of the non-rectified probe output signal 240 could be instead counted over a predetermined time interval using well known zero crossing selection circuitry.

Figure 15B:
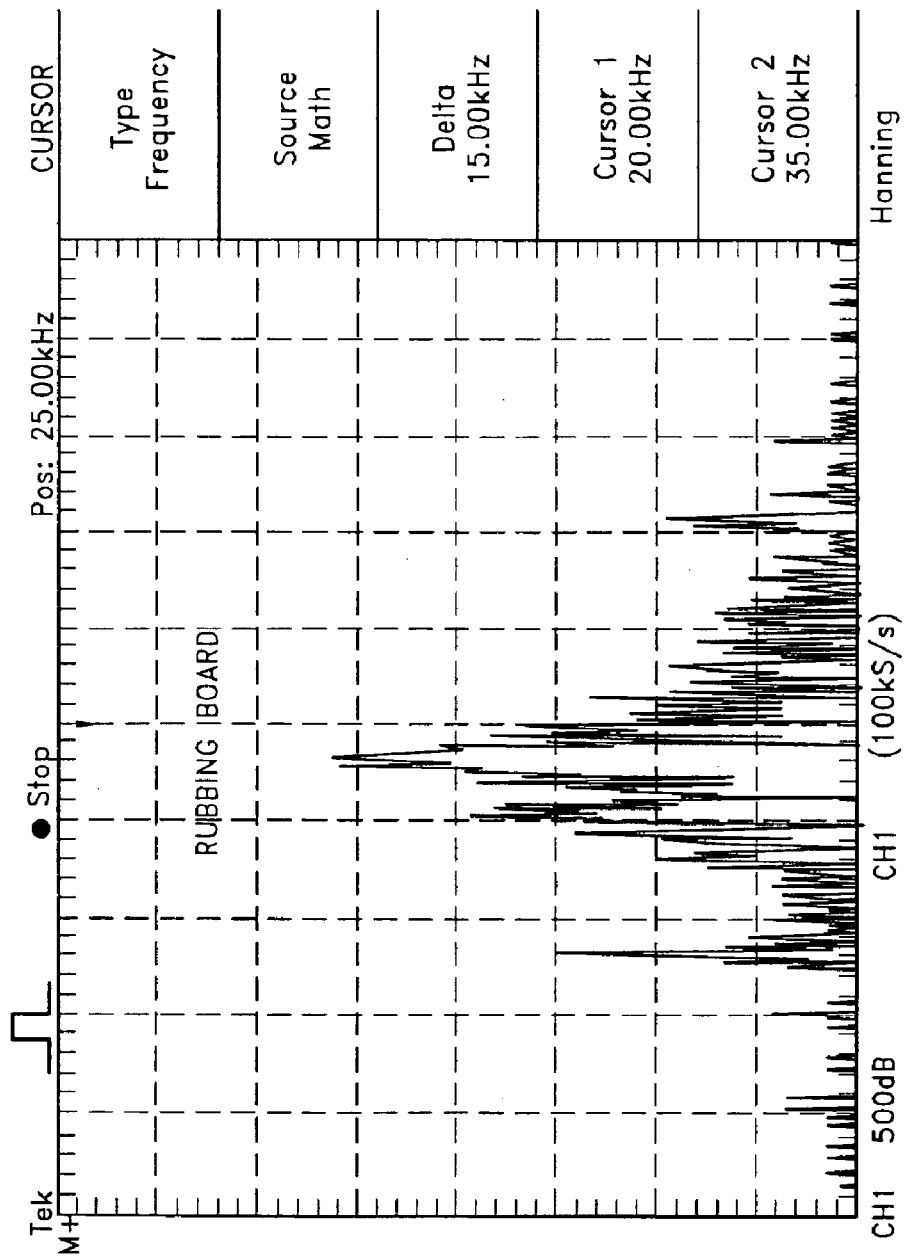
FIG. 15B graphically illustrates the output signals produced by the transducers from another extraneous noise source (rubbing the board)

A major problem in acoustically detecting termites or other wood-feeding insects is distinguishing acoustic emission created by the insects and acoustic emission created by extraneous noise sources. This problem is exacerbated by the fact that the noise emissions are generally greater in amplitude than the insect-created emissions as illustrated in FIGS. 15A, 15B and 15C which graphically illustrate the relative magnitudes of acoustic emission detected from insect activity (FIG. 15C) and noise (FIGS. 15A and 15B).

Figure 15C:
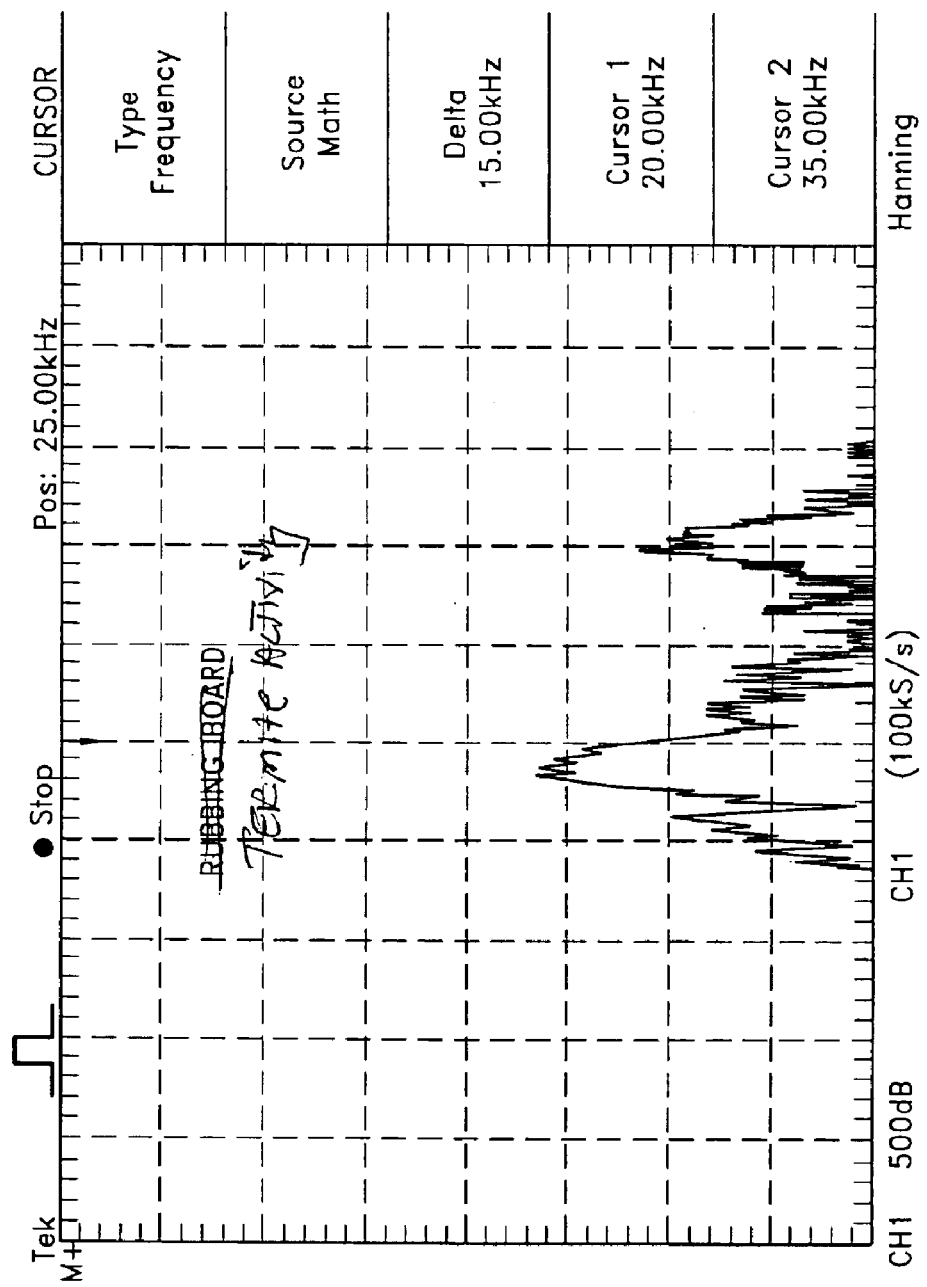
FIG. 15C graphically illustrates the output signals produced by the transducer from termite activity.

FIG. 15C shows the frequency response of actual termite activity in a wooden board detected using the transducer detector 20 described above and averaged over 126 samples. Two distinct frequency bands at approximately 25 KHz and 35 KHz frequencies contain most of the energy of the signal from the termite activity. The lack of any signals below 20 KHz is due to the presence of a 20 KHz hi-pass filter.

FIG. 15C shows the detected frequency content using the transducer 20 and averaged over 126 signals that is produced by gently rubbing the wooden board with the index finger near the transducer location. This rubbing could also be audibly detected at 1 meter away from the transducer. The low frequency content of the signals matches that of the termite activity but there is a lack of signals at the higher frequency compared to the termite activity. The average amplitude of the low frequency signals are 10 dB higher than that from the termite activity illustrated in FIG. 15C.

FIG. 15A shows the frequency spectra produced by jingling of car keys 1 meter away from the transducer 20. Again, there is a shift to lower frequencies in comparison to the termites and rubbing, and a lack of higher frequency content. Here again the amplitude of the low frequency signals appear to be approximately 10 dB higher than the amplitude produced by the termites. Jingling of the car keys at 30 feet distance from the transducer could still be easily detected by the system.

Figure 14A:
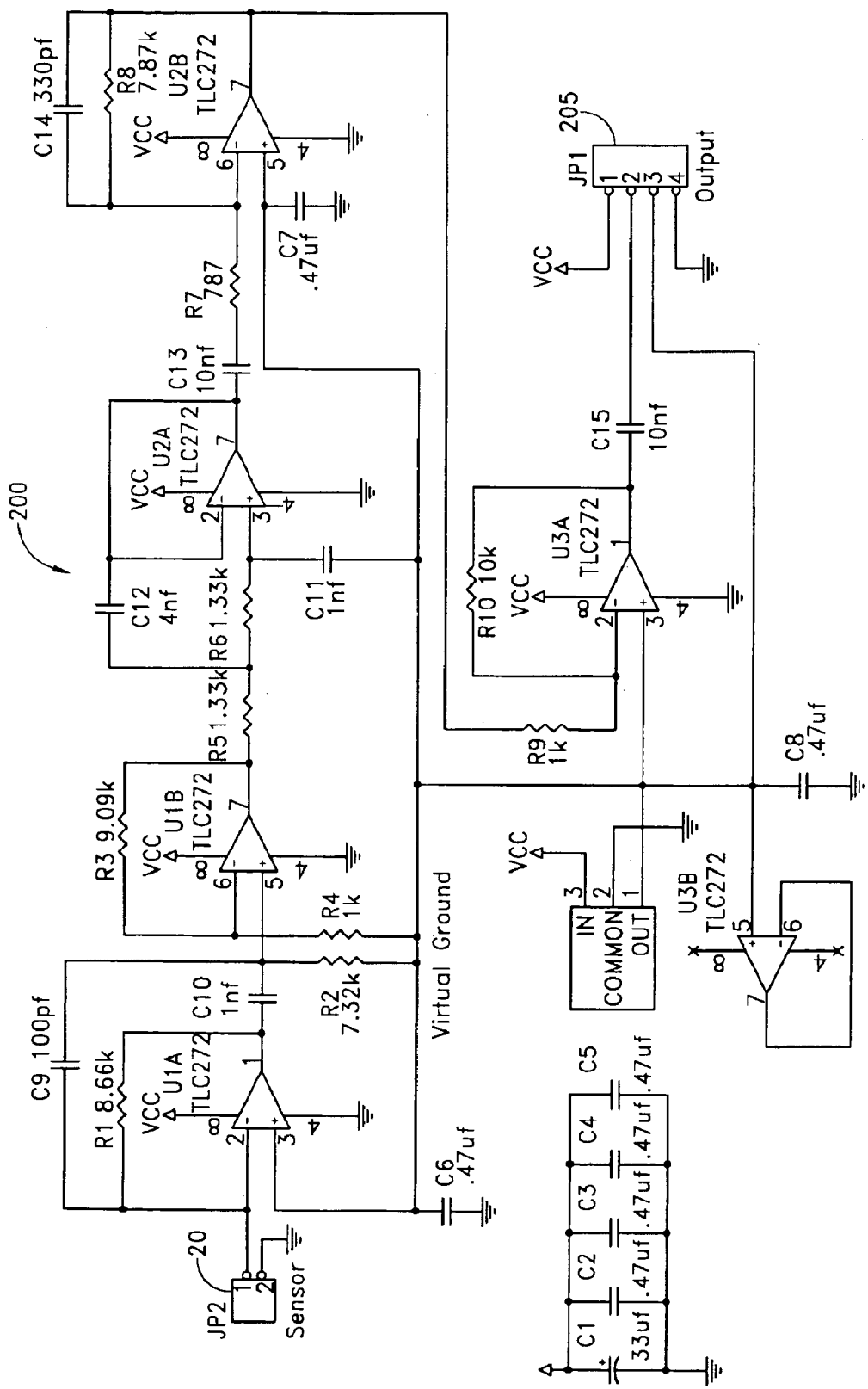
FIG. 14A is an electrical schematic of the pre-amplifier stages shown in FIG. 13.
Figure 14B:
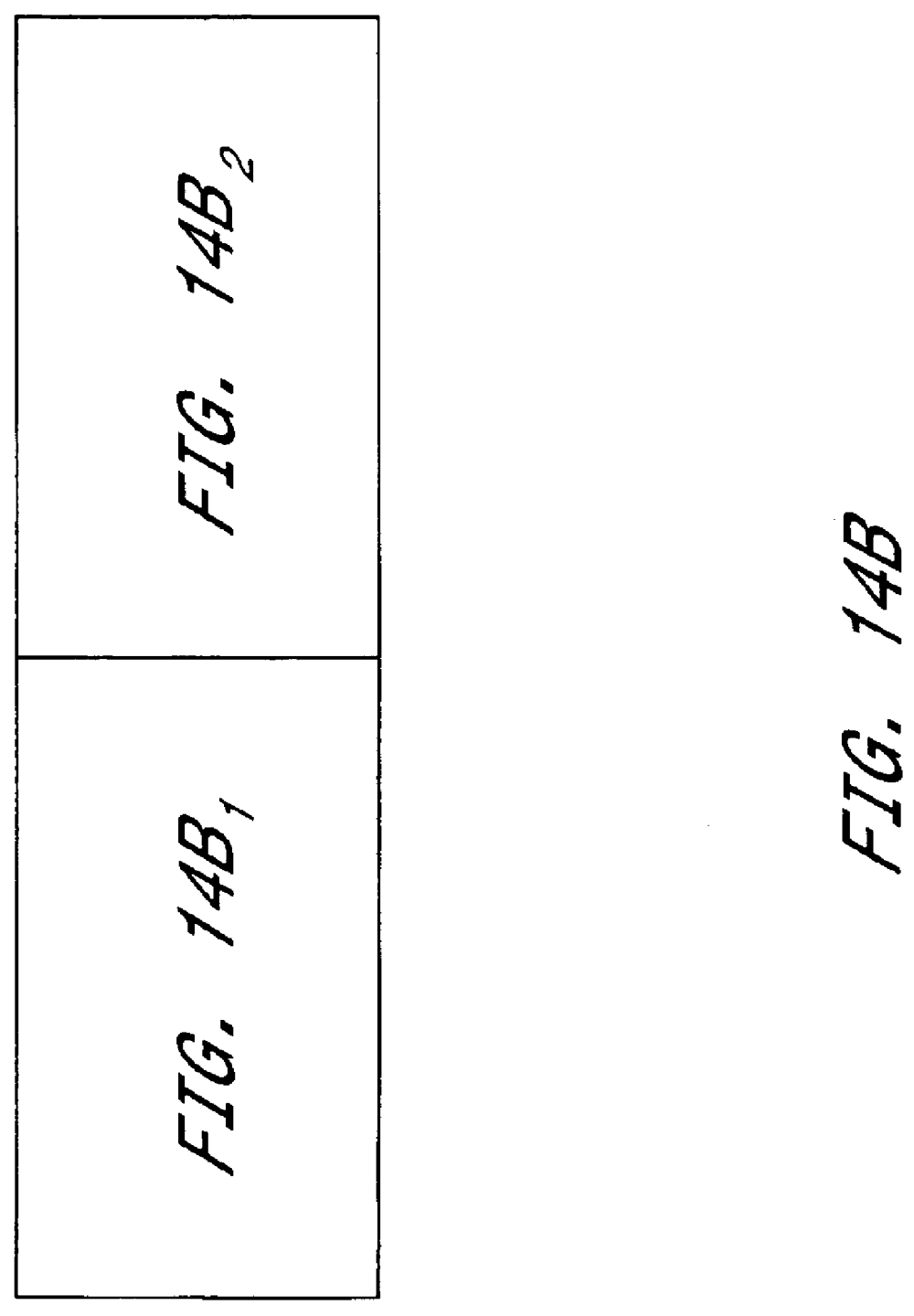
Figure 16:
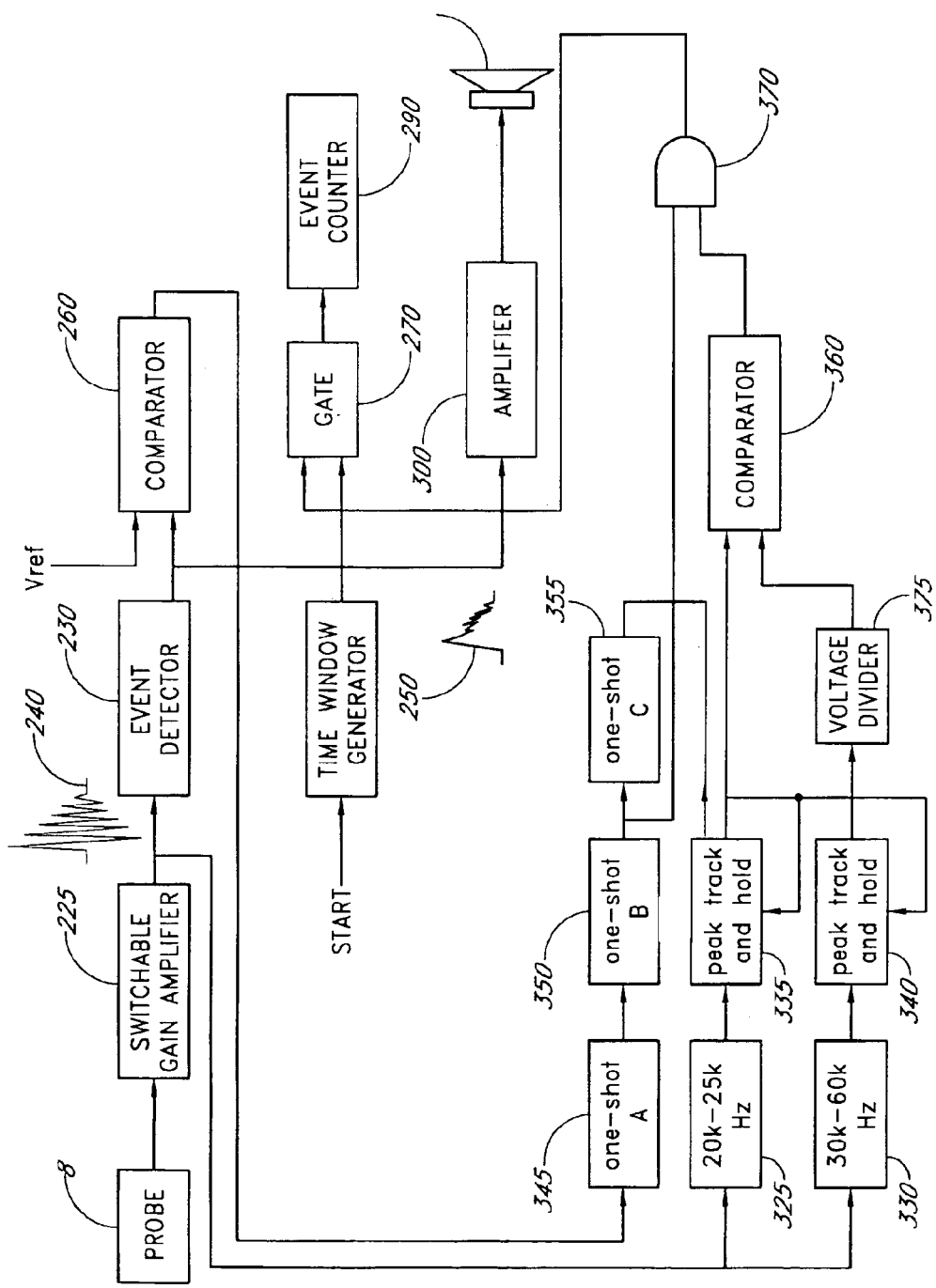
FIG. 16 is a block diagram of another embodiment of the probe and signal processing circuitry.

Another embodiment of the signal processing circuitry is shown in FIGS. 14A, 14B and 16. For convenience, those blocks of these figures which may be the same as those shown in FIG. 13, are given the same identification numerals.

In this embodiment, the signal outputs of transducer 20 are processed through low frequency bands of 20–25 KHz (LF) and high frequency bands of 25–50 KHz (HF) filters and the ratio of the HF/LF amplitudes used to eliminate the extraneous noise signals produced by Out-Of-Plane (OOP) sources. The ratios HF/LF in these frequency bands are higher for signals produced by termite activity than from signals due to noise sources, thereby substantially increasing the sensitivity of the system to termite activity.

Referring now to FIG. 16, the output of switchable gain amplifier 225 is respectively connected to the input of LF bandbase (20 KHz–25 KHz) filter 325 and HF bandpass (25 KHz–50 KHz) filer 330. The peak amplitudes of frequency components in the LF and HF frequency bands are provided by respective peak track and hold circuitry 335, 340 controlled by series connected one-shot multivibrators 345, 350 and 355 each typically having a cycle of about one millisecond. The output peaks are compared in comparator 360 and the ratio fed through gate 370 to the input of gate 270 to be audibly detected in the manner described above with reference to FIG. 12. It has been determined experimentally that dividing the peak amplitudes of frequency components in the 25 KHz to 50 KHz range of frequencies by the peak amplitudes of frequency components in the 20 KHz to 25 KHz range of frequencies for termite activity gives a HF/LF ratio predominately above a value of 2 with occasional values below 2. The noise sources such as keys jingling, rubbing of the surface and impact produce a HF/LF ratio of approximately 1 with occasional values exceeding 1.5. Therefore, selecting a set ratio of about 2 for the ratio filter substantially completely eliminates signals from acoustic noise sources. Voltage divider 375 enables setting this ratio so that signals producing a ratio of 2 or greater are accepted as valid termite produced signals.

Multiple Channel Operation

An acoustic emission instrument that has the capability of filtering out extraneous noise sources such as impact, friction, and airborne signals will fulfill two primary needs: One, locating termites or other wood feeding insects where there is no visual evidence of their presence, and two, monitoring of treatment processes to eradicate such insects to assure that the treatment process has been effective. For many situations involving local treatment, a portable battery powered unit can be effective in solving both of the above needs. In other situations involving tenting of large structures, which prohibit the presence of human occupancy, the ability to monitor many locations within the structure while the treatment is in process is desired. For this situation, the multiplexing of many channels placed at strategic locations throughout the structure would be an effective method to determine how long the treatment should take to eradicate the insects.

Figure 17:
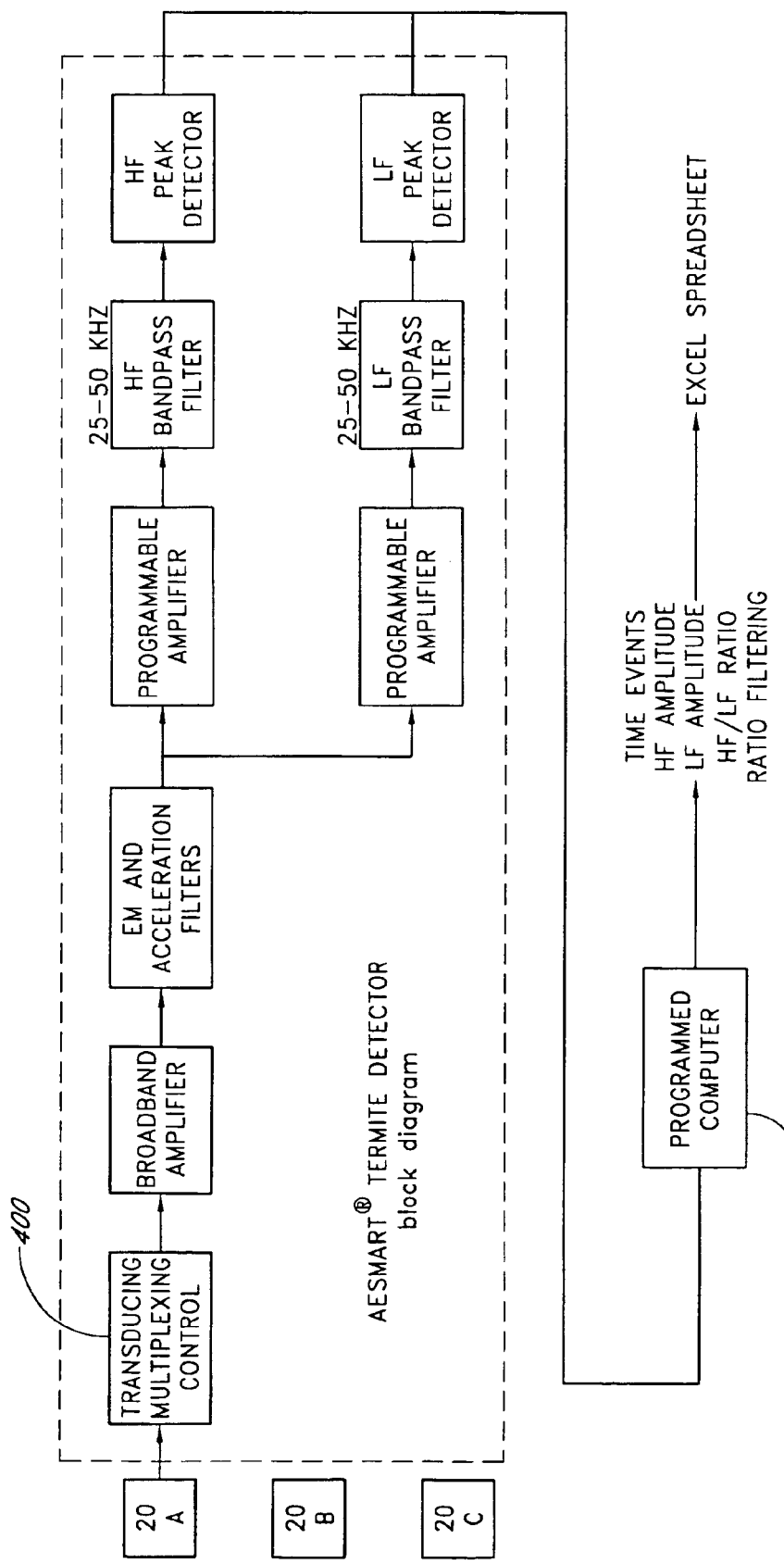
FIG. 17 is a block diagram of a multiple channel termite detection system.

A block diagram of a multiple channel system to accomplish the effective monitoring of many locations is shown in FIG. 17. Transducers 20A, 20B and 20C are representative of a plurality of transducers 20 which can number as many as one hundred or more. These transducers may be in direct contact with the structure being treated or mounted on waveguides 10 that are within bore holes placed in termite-infested locations throughout a large structure. All of them are connected by a single cable or otherwise to a multiplexor 400, with each transducer having an address that is addressable by the computer 410 for monitoring and recording of data from each specific location. The cable is then taken to a van or other vehicle which contains the hardware and computer for analyzing the data. A dwell time is selected by the operator and the system sequentially addresses each transducer 20 and records data from each channel based on the selected dwell time. As described above, the signal from the termite activity is split into two frequency components, the peak amplitude of each channel is measured and the ratio calculated by the computer. A ratio filter eliminates extraneous noise as described above. In one embodiment, the filtered data is downloaded to an excel spread sheet shown in FIG. 18 to allow analysis and plotting of each channel's data.

One example of use of a multiple channel system is a house or home that is tented and filled with poisonous gas. Other treatment procedures commonly used are heating and cooling, which may be also used for a localized treatment making the use of a single or few probes. All transducers are monitored during the treatment process. If activity is recorded from any transducer after the normal treatment process is complete, the treatment process should be repeated.

Although the present invention has been described in terms of a certain preferred embodiments, other embodiments apparent to those of ordinary skill in the art also are within the scope of this invention. Thus, various changes and modifications may be made without departing from the spirit and scope of the invention. Moreover, not all of the features, aspects and advantages are necessarily required to practice the present invention. Accordingly, the scope of the present invention is intended to be identified only by the claims

What is claimed is:

1. An apparatus for detecting the movement of insects comprising acoustic emission means including a waveguide for detecting the in-plane, ultrasonic signals generated by the movement of insects in wood and producing electrical signals therefrom, means for processing said electrical signals into a high frequency band (HF) and a low frequency band (LF) and dividing the peak amplitudes of signals within said high frequency band with the peak amplitudes of signals within said low frequency band to produce a HF/LF ratio indicative of movement of said insects.

2. The apparatus of claim 1 wherein said high frequency band (HF) signals are in substantially the range of 25 KHz to 50 KHz.

3. The apparatus of claim 1 wherein said low frequency band (LF) signals are in substantially the range of 20 KHz to 25 KHz.

4. The apparatus of claim 1 wherein said HF/LF ratio is indicative of said insects feeding on said wood.

5. The apparatus of claim 1 including means for selecting a HF/LF ratio of about 2 or greater to substantially eliminate extraneous signals.

6. The apparatus of claim 1 including means for selecting a HF/LF ratio greater than 2 as valid insect produced signals.

7. The apparatus of claim 1 wherein said insects are termites.

* * * * *